United States Patent
Taniguchi

(10) Patent No.: US 7,235,171 B2
(45) Date of Patent: Jun. 26, 2007

(54) HYDROGEN SENSOR, HYDROGEN SENSOR DEVICE AND METHOD OF DETECTING HYDROGEN CONCENTRATION

(75) Inventor: Noboru Taniguchi, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 419 days.

(21) Appl. No.: 10/202,265

(22) Filed: Jul. 23, 2002

(65) Prior Publication Data

US 2003/0024813 A1    Feb. 6, 2003

(30) Foreign Application Priority Data

Jul. 24, 2001  (JP) .............................. 2001-223309
Sep. 19, 2001  (JP) .............................. 2001-285903

(51) Int. Cl.
*G01N 27/407* (2006.01)
(52) U.S. Cl. ..................... 205/787; 204/424; 204/426
(58) Field of Classification Search ............... 204/421, 204/424, 426; 73/19.01, 23.31; 205/787
See application file for complete search history.

(56) References Cited

U.S. PATENT DOCUMENTS

| | | | |
|---|---|---|---|
| 5,935,398 A | * | 8/1999 | Taniguchi et al. .......... 204/424 |
| 6,419,808 B1 | * | 7/2002 | Taniguchi .................. 204/424 |
| 6,793,788 B2 | * | 9/2004 | Wang et al. ................ 204/424 |

FOREIGN PATENT DOCUMENTS

| | | | |
|---|---|---|---|
| EP | 1029837 A2 | * | 8/2000 |
| EP | 1 041 380 A2 | * | 10/2000 |
| JP | 63-94146 | | 5/1988 |
| JP | 1-265152 A | * | 10/1989 |
| JP | 4-34356 | | 2/1992 |
| JP | 8-327592 | | 12/1996 |

OTHER PUBLICATIONS

CAPLUS abstract for Wang et al, Huaxue Xuebao (2004), 62(23), pp. 2287-2291.*
Hibino et al. "Galvanic Cell Type Hydrocarbon Sensor Using a High Temperature-Type Protonic Conductor" The Meeting Abstract of the 61st Symposium Electrochemical Society in Sendai, p. 99, 1994.
Inaba et al. "Limiting-Current Sensor Using Proton Conductor Thin-Film" The proceedings of the autumn conference of the chemical sensors society, Toyota Central R&D lab., Inc., pp. 145-148, abstract only, 1995.
Japanese Office Action from the corresponding JP 2002-206092, mailed Feb. 6, 2007, untranslated.

* cited by examiner

*Primary Examiner*—Kaj K. Olsen
(74) *Attorney, Agent, or Firm*—Hamre, Schumann, Mueller & Larson, P.C.

(57) ABSTRACT

A hydrogen sensor includes a solid electrolyte made of a barium cerium oxide, and a first electrode and a second electrode that are formed on the surface of the solid electrolyte. The first and the second electrodes are made of a material having a catalytic effect with respect to an oxidation reaction of hydrogen and are made of the same material. Thus, the hydrogen sensor can be inexpensive and has good hydrogen selectivity and responsiveness to detection, and thus it is possible to measure hydrogen in a high concentration region.

7 Claims, 19 Drawing Sheets

HYDROGEN SENSOR, HYDROGEN SENSOR DEVICE AND METHOD OF DETECTING HYDROGEN CONCENTRATION

BACKGROUND OF THE INVENTION

1. Field of the Invention

The present invention relates to a hydrogen sensor.

2. Description of the Related Art

To detect hydrogen with a high sensitivity, sensors of various systems such as optical sensors, catalytic combustion sensors, semiconductor sensors, electromotive force type sensors, current detection (battery) sensors, mechanical type sensors utilizing pressure variation that employ hydrogen adsorption or hydrogen occlusion characteristics, and MOS capacitor sensors have been developed and used in different applications in which the characteristics of each system can be exhibited sufficiently. For example, to detect gas leakage, semiconductor sensors made of a material such as $TiO_2$, $SnO_2$ or the like generally are used. For gas leakage of industrial or combustion equipment or temperature control, catalytic combustion sensors generally are used.

In recent years, hydrogen sensors made of, for example, $SrCeYO_3$, which is a proton conductor, have been developed as a sensor that can detect hydrogen in a solution in which Al or the like is molten at a high temperature.

Furthermore, a sensor using a calcium-zirconium oxide, which is an oxide ion conductor (oxide ions are represented by $MO^-$, $MxOy^{\alpha-}$ or the like, in addition to $O^{2-}$) for a solid electrolyte, is known as a hydrocarbon sensor that detects combustible gas, which is the same as a hydrogen sensor. This sensor is characterized by excellent hydrogen selectivity, although the configuration is simple. For example, electromotive force type sensors employing Pd-Au electrodes (see the Meeting Abstract of the Spring Meeting of the Electrochemical Society '95, University of Nagoya) and limiting a current detection type sensors employing porous alumina as a diffusion controlled layer (see the proceedings of the autumn conference of the Chemical Sensor Society '96, TOYOTA Central R&D Lab., Inc.) are well known.

Thus, a proton conductor such as a $SrCeO_3$-based oxide and a $CaZrO_3$-based oxide, or an oxide ion conductor such as zirconia and ceria is used as an ion conductor that is used for a solid electrolyte, and various hydrogen sensors with high sensitivity and high hydrogen selectivity have been proposed.

However, inexpensive hydrogen sensors that have excellent hydrogen selectivity and can measure hydrogen even in a high concentration region have not been developed. For example, optical sensors are suitable for precise analysis, but they are expensive.

Although catalytic combustion sensors and semiconductor sensors are comparatively inexpensive and have high reliability during measurement for a long time, they have poor hydrogen selectivity because they react with a reducing gas such as CO that is not an immediate subject for measurement, so that they are not suitable for detection of a high concentration of % order. Furthermore, in semiconductor sensors, the hydrogen selectivity is increased by mixing a semiconductor material used with a catalytically active material, but they are not suitable for measurements for high concentration regions.

In electromotive force type sensors and a current detection type sensors employing a calcium-zirconium oxide, which is an oxide ion conductor, for a solid electrolyte, the detection precision of hydrogen concentrations depends on the characteristics of the ion conductor. In addition, the proton conductivity of the ion conductor is small (about $5 \times 10^{-4}$ S/cm at 600° C.), and the detection precision of hydrogen concentrations is low. Therefore, for electromotive force type sensors, it is necessary to set the temperature of a sensor to a high temperature of 700° C. or more during detection of hydrogen concentrations, and for a current detection type sensors, it is necessary to reduce the thickness of the solid electrolyte. Mechanical type sensors utilizing pressure variation and MOS capacitor sensors have poor responsiveness to detection, and low practical values.

At present, there is a demand for hydrogen sensors for detecting hydrogen in living environments, selectively detecting hydrogen leaked from a fuel battery, and detecting the concentration of hydrogen contained in the air at room temperature or hydrogen in an airtight room. In particular, inexpensive hydrogen sensors that have excellent hydrogen selectivity and good responsiveness and can detect hydrogen in a high concentration region in a simple manner are desired as a sensor for controlling a fuel battery and equipment utilizing hydrogen, but as described above, hydrogen sensors that satisfy these requirements sufficiently have not been obtained yet.

SUMMARY OF THE INVENTION

Therefore, with the foregoing in mind, it is an object of the present invention to provide an inexpensive hydrogen sensor that has good hydrogen selectivity and responsiveness in detection and can detect hydrogen in a high concentration region.

A hydrogen sensor of the present invention includes a solid electrolyte; and a first electrode and a second electrode that are formed on the surface of the solid electrolyte. The solid electrolyte includes an ion conductor that conducts protons and oxide ions, and the first electrode and the second electrode are made of a material having a catalytic effect with respect to an oxidation reaction of hydrogen and made of the same material.

According to another aspect of the present invention, a hydrogen sensor includes a solid electrolyte; and a first electrode and a second electrode that are formed on the surface of the solid electrolyte. The solid electrolyte includes an ion conductor that conducts protons and oxide ions, and the first electrode is capable of preventing oxygen from being ionized.

According to another aspect of the present invention, a hydrogen sensor includes a solid electrolyte; and a first electrode and a second electrode that are formed on the surface of the solid electrolyte. The solid electrolyte includes an ion conductor that conducts protons and oxide ions. The first electrode is capable of preventing oxygen from being ionized. The second electrode is made of a material having a catalytic effect with respect to an oxidation reaction of hydrogen.

According to another aspect of the present invention, a hydrogen sensor includes a solid electrolyte; a first electrode and a second electrode that are formed on the surface of the solid electrolyte; and controlling means for controlling the amount of hydrogen that reaches the second electrode. The solid electrolyte includes an ion conductor that conducts protons and oxide ions, and both the first and the second electrodes are made of a material having a catalytic effect with respect to an oxidation reaction of hydrogen.

According to another aspect of the present invention, a hydrogen sensor includes a solid electrolyte; a first electrode and a second electrode that are formed on the surface of the solid electrolyte, controlling means for controlling the amount of hydrogen that reaches the second electrode. The solid electrolyte includes an ion conductor that conducts protons and oxide ions. At least one of the first and the second electrodes is capable of preventing oxygen from being ionized.

It is another object of the present invention to provide an inexpensive and high performance hydrogen sensor that has good hydrogen selectivity and responsiveness to detection, can measure hydrogen in a high concentration region, in which the leak current is stabilized during detection of a hydrogen concentration, and the drift amount of a sensor output is reduced.

According to another aspect of the present invention, a hydrogen sensor includes a solid electrolyte; and a first electrode and a second electrode that are formed on the surface of the solid electrolyte. The solid electrolyte is made of an ion conductor that conducts protons and oxide ions. The temperature of the sensor at the time of the detection of a hydrogen concentration is 300° C. or more. The electrolytic field intensity formed in the solid electrolyte by the first and the second electrodes is 1.11 V/mm or less.

DESCRIPTION OF THE PREFERRED EMBODIMENTS

Hereinafter, embodiments of the present invention will be described with reference to the accompanying drawings.

Embodiment 1

Figure 1A:
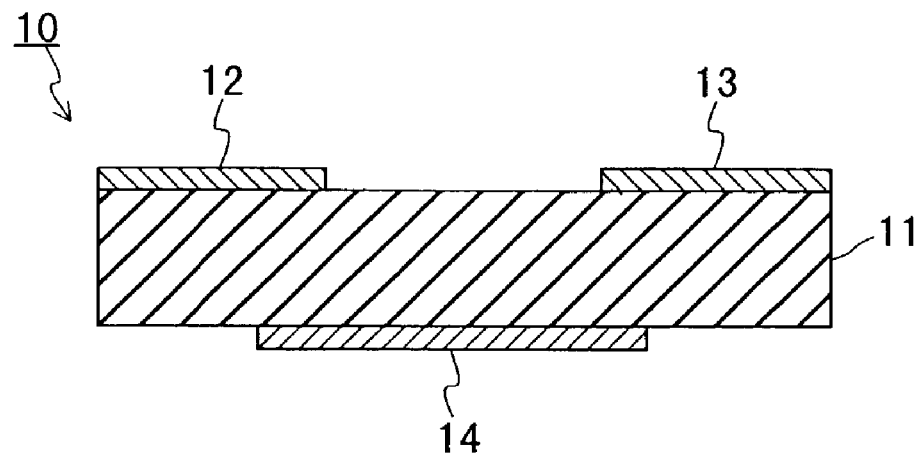
FIG. 1A is a cross-sectional view showing the structure of a hydrogen sensor of Embodiment 1.
Figure 1B:
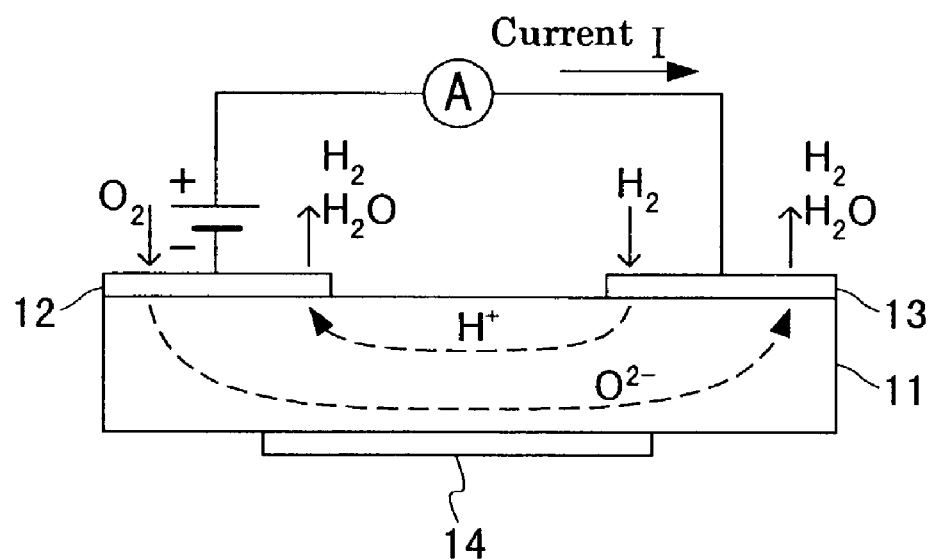
FIG. 1B is a schematic view showing the operation of the hydrogen sensor of Embodiment 1.

FIG. 1A shows a cross-sectional view of the structure of a hydrogen sensor 10 of this embodiment, and FIG. 1B is a schematic view showing the operation operation thereof. A solid electrolyte 11 is made of an ion conductor that conducts protons ($H^+$) and oxide ions ($O^{2-}$). A first electrode 12 and a second electrode 13 are formed on the surface of the solid electrolyte 11 to conduct ions in the solid electrolyte 11, and a heater 14 for heating the solid electrolyte 11 is provided on the lower surface thereof The heater 14 can be made of sintered platinum that has been patterned, for example.

The hydrogen sensor 10 is a so-called a current detection type sensor, and a constant voltage is applied between the first electrode 12 and the second electrode 13 so that a current generated by the conduction of oxide ions flows steadily between the first electrode 12 and the second electrode 13, and a current generated by protons is added thereto, and a current value that has changed is measured so that the hydrogen concentration of a gas to be measured is detected.

For the solid electrolyte 11, oxides containing barium and cerium, for example, barium-cerium oxides can be used. The barium-cerium oxides can contain at least one selected from the group consisting of zirconium, gadolinium, ytterbium, and indium. Examples of the barium-cerium oxides include sintered $BaZr_{0.4}Ce_{0.4}In_{0.2}O_{3-\alpha}$, $BaZr_{0.6}Ce_{0.2}Gd_{0.2}O_{3-\alpha}$, $BaCe_{0.8}Gd_{0.2}O_{3-\alpha}$, $BaZr_{0.4}Ce_{0.4}Gd_{0.2}O_{3-\alpha}$, $BaZr_{0.4}Ce_{0.4}Yb_{0.2}O_{3-\alpha}$, $BaZr_{0.2}Ce_{0.65}Gd_{0.15}O_{3-\alpha}$, $BaCe_{0.9}Gd_{0.1}O_{3-\alpha}$, $BaZr_{0.5}Ce_{0.3}Gd_{0.2}O_{3-\alpha}$, $BaZr_{0.6}Ce_{0.2}Nd_{0.2}O_{3-\alpha}$, $BaZr_{0.2}Ce_{0.65}In_{0.15}O_{3-\alpha}$, $BaCe_{0.85}Gdo_{0.15}O_{3-\alpha}$, $BaZr_{0.52}Ce_{0.24}Gdo_{0.24}O_{3-\alpha}$, $BaZr_{0.6}Ce_{0.2}Y_{0.2}O_{3-\alpha}$, $BaZr_{0.3}Ce_{0.5}In_{0.2}O_{3-\alpha}$, $BaZr_{0.56}Ce_{0.24}Gd_{0.2}O_{3-\alpha}$, and $BaZr_{0.3}Ce_{0.5}In_{0.2}O_{3-\alpha}$, where α represents the deficiency of oxygen. These substances can be expressed by a general formula $BaCe_{1-X-Y}L_XM_YO_{3-\alpha}$, where L is a tetravalent element, M is a trivalent element, and $0 \leq X < 1$, $0 \leq Y < 1$, and $\alpha = 1/2\, Y$. For the element L, Zr or Hf can be used, and for the element M, rare earth elements can be used.

The first electrode 12 and the second electrode 13 are made of a material having a catalytic effect with respect to an oxidation reaction of hydrogen and are made of the same material. More specifically, a metal containing at least one selected from the group consisting of platinum, gold, silver, palladium, and ruthenium can be used, and for example, a pure metal of platinum, gold, silver, palladium or ruthenium can be used. The first electrode 12 and the second electrode 13 can be formed by firing a metal paste, physical methods such as sputtering, or CVD (chemical vapor deposition method).

In the hydrogen sensor 10 of this embodiment, when a constant voltage is applied between the first electrode 12 as the cathode and the second electrode 13 as the anode, the hydrogen contained in a gas to be measured is dissociated in the second electrode 13, becomes protons, is conducted in the solid electrolyte 11, becomes hydrogen or water in the first electrode 12, and is released. On the other hand, the oxygen contained in the gas to be measured is degraded in the first electrode 12, becomes oxide ions, is conducted in the solid electrolyte 11, becomes hydrogen or water in the second electrode 13, and is released. Thus, charges move in the solid electrolyte 11 in the form of protons and oxide ions, so that a current flows. See FIG. 1B.

In this case, the magnitude of a current that has varied with a hydrogen concentration can be changed by changing a material used for the first electrode 12 and the second electrode 13 as appropriate. The variation of the current can be classified into the following two cases. When a current generated by the conduction of oxide ions flows steadily, a current generated by the conduction of protons is added thereto, so that the current value is increased; and when a current generated by the conduction of oxide ions flows steadily, hydrogen is oxidized by a catalyst on the side of the cathode, and the conduction of oxide ions is decreased, so that the current value is decreased.

Hereinafter, the results of measuring hydrogen concentrations in the air with the hydrogen sensor 10 of this embodiment will be described. Herein, sintered $BaZr_{0.4}Ce_{0.4}In_{0.2}O_{3-\alpha}$ and sintered $BaZr_{0.6}Ce_{0.2}Gd_{0.2}O_{3-\alpha}$ were used for the solid electrolyte 11. The size of the solid electrolyte 11 was 10 mm square and 0.5 mm in thickness. The first electrode 12 and the second electrode 13 were formed by firing a platinum paste.

Figure 2:
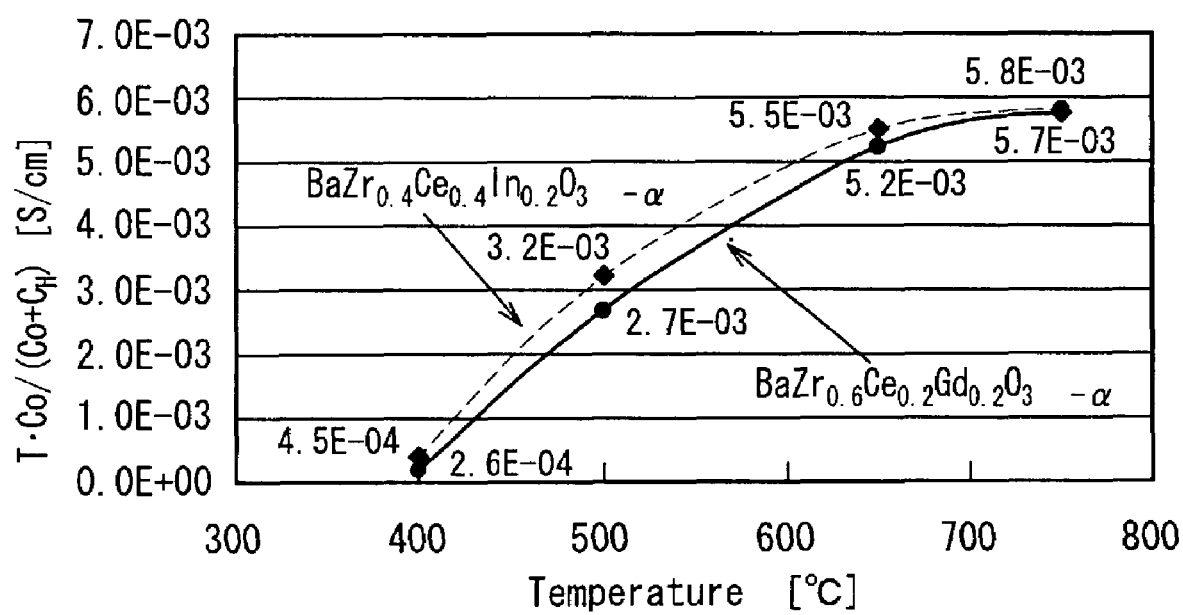
FIG. 2 is a graph showing an example of the relationship between the value of $T \cdot C_0/(C_0+C_H)$ and the temperature in the hydrogen sensor of Embodiment 1.

FIG. 2 shows the relationship between the temperature (° C.) and the value of $T \cdot C_0/(C_0+C_H)$ (S/cm) obtained by multiplying the conductivity T (S/cm) of the solid electrolyte 11 by the ratio in conductance between oxide ions and protons $C_0/(C_0+C_H)$ ($C_0$: the conductance of the oxide ions(S/cm), and $C_H$: the conductance of the protons(S/cm)), with respect to the cases where the sintered $BaZr_{0.4}Ce_{0.4}In_{0.2}O_{3-\alpha}$ is used and where the sintered $BaZr_{0.6}Ce_{0.2}Gd_{0.2}O_{3-\alpha}$ is used for the solid electrolyte 11. These results indicate that as the temperature increases, the value of $T \cdot C_0/(C_0+C_H)$ increases in both the materials.

Figure 3:
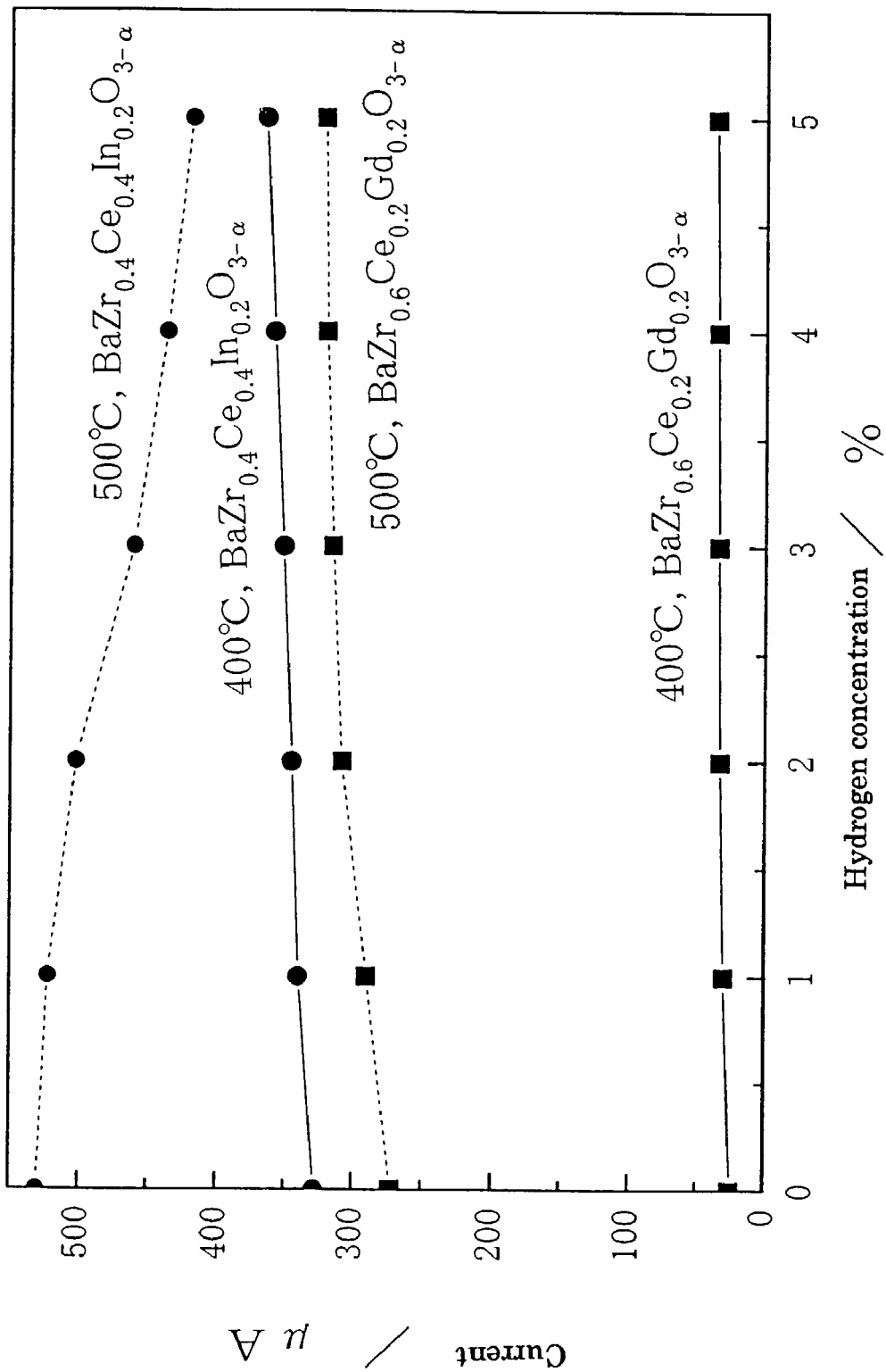
FIG. 3 is a graph showing the relationship between the hydrogen concentration and the current value in the hydrogen sensor of Embodiment 1.

FIG. 3 shows the relationship between the current flowing between the first electrode 12 and the second electrode 13 and the hydrogen concentration of a gas to be measured in the case where the air containing 10 vol % of oxygen is used as the gas to be measured and $T \cdot C_0/(C_0+C_H) \leq 2.7 \times 10^{-3}$ (S/cm) is satisfied. When the conductance of protons is larger than that of oxide ions, the increase of the current value caused by the conduction of protons is dominant, and as the hydrogen concentration increases, the current value increases.

Figure 4:
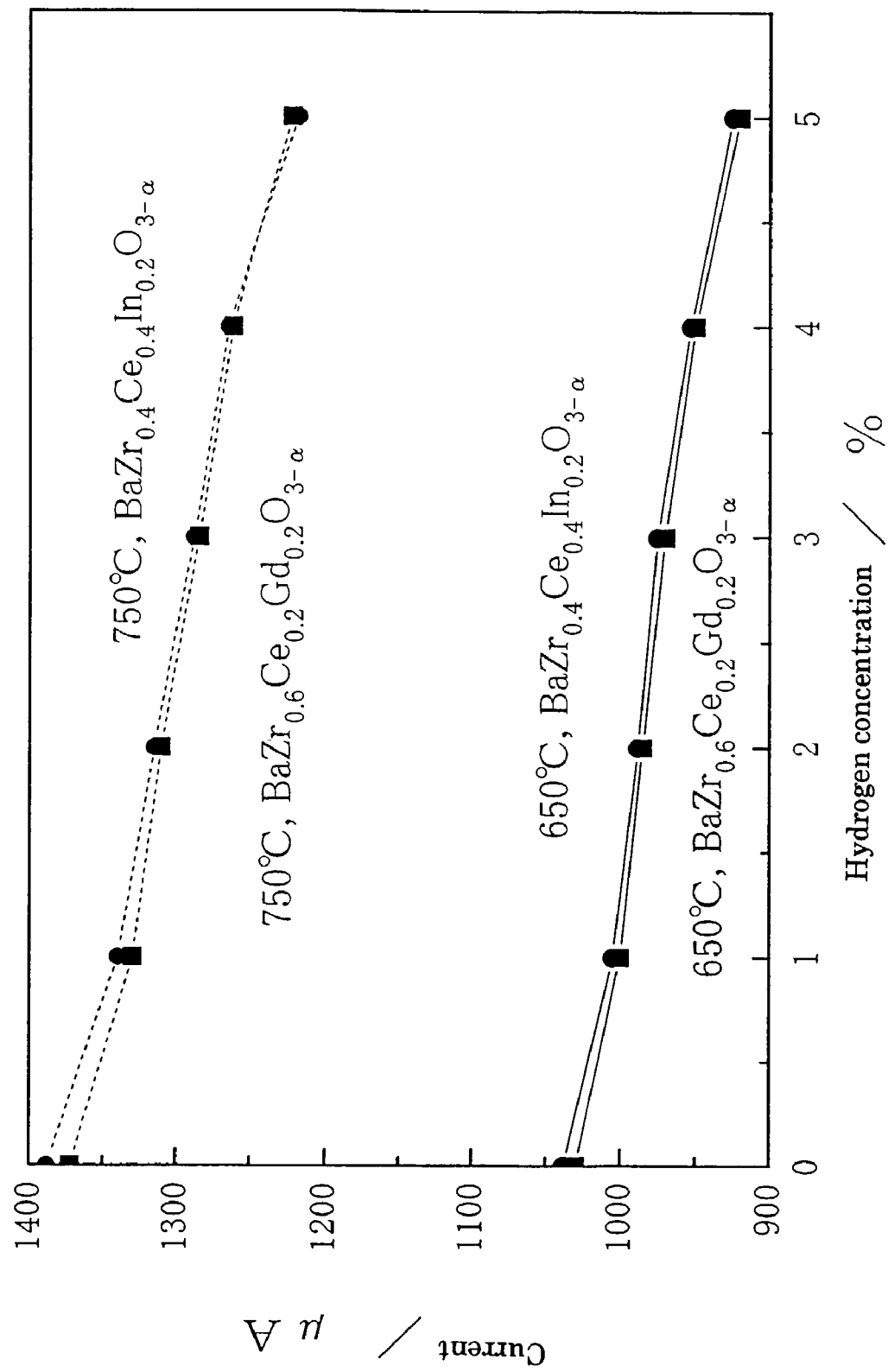
FIG. 4 is a graph showing the relationship between the hydrogen concentration and the current value in the hydrogen sensor of Embodiment 1.

FIG. 4 shows the relationship between the current flowing between the first electrode 12 and the second electrode 13 and the hydrogen concentration of a gas to be measured in the case where the air containing 10 vol % of oxygen is used as the gas to be measured and $T \cdot C_0/(C_0+C_H) \geq 3.2 \times 10^{-3}$ (S/cm). When the conductance of protons is smaller than that of oxide ions, the decrease of the current value caused by the conduction of oxide ions is dominant, and as the hydrogen concentration increases, the current value decreases (the temperature in the horizontal axis in FIG. 2 and the temperatures shown in FIGS. 3 and 4 are the temperature of the sensor at the time of the detection of the hydrogen concentration). As for the responsiveness, the time until the current value reaches 90% of the final current value was about 10 seconds, which is a good responsiveness.

As described above, in the hydrogen sensor 10, whether the current value to be detected increases or decreases as the hydrogen concentration of the gas to be measured increases is determined not by the type of the solid electrolyte or the temperature of the atmosphere, but $T \cdot C_0/(C_0+C_H)$.

Furthermore, in this embodiment, in order to investigate the influence of the mixture of other types of gases, 2 vol % each of methane, ethane, propane, butane, carbon monoxide, nitrogen monoxide, carbon dioxide, and water vapor saturated at room temperature were added to the gas to be measured, and an increase or a decrease of the current value was observed. Then, at an atmospheric temperature of 600° C. or less, there was substantially no variation in the current value, and the current values measured were very stable.

The hydrogen sensor 10 of this embodiment can detect stably and easily hydrogen in a high concentration region of 0 to 5 vol % in the presence of oxygen in the air with excellent responsiveness and hydrogen selectivity. Furthermore, the hydrogen sensor 10 is inexpensive because of its simple structure, and has high reliability.

Embodiment 2

Figure 5A:
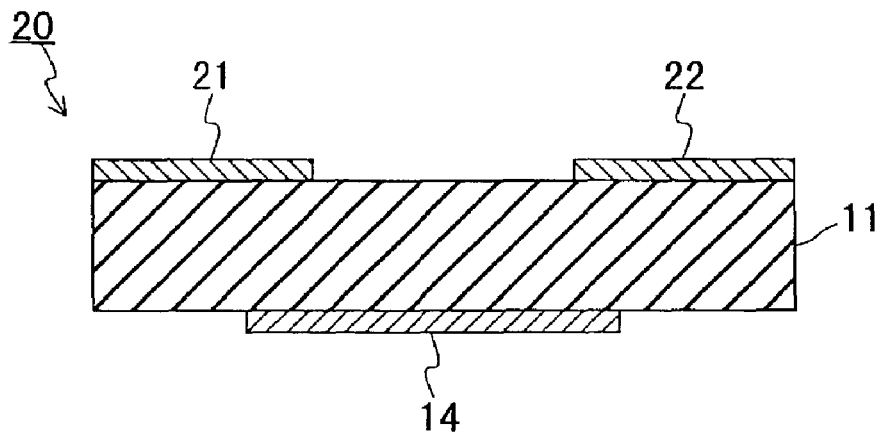
FIG. 5A is a cross-sectional view showing the structure of a hydrogen sensor of Embodiment 2.
Figure 5B:
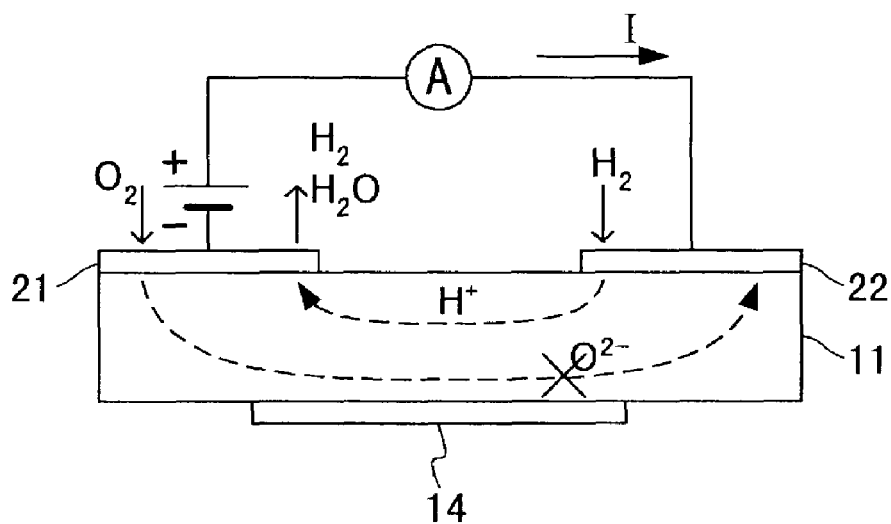
FIG. 5B is a schematic view showing the operation of the hydrogen sensor of Embodiment 2.

FIG. 5A shows a cross-sectional view of the structure of a hydrogen sensor 20 of this embodiment, and FIG. 5B is a schematic view showing the operation thereof. A solid electrolyte 11 is made of an ion conductor that conducts protons ($H^+$) and oxide ions ($O^{2-}$). A first electrode 21 and a second electrode 22 are formed on the surface of the solid electrolyte 11 to conduct ions in the solid electrolyte 11, and a heater 14 for heating the solid electrolyte 11 is provided on the lower surface thereof. The heater 14 can be made of sintered platinum that has been patterned, for example.

The hydrogen sensor 20 is a so-called a current detection type sensor like the hydrogen sensor 10 in Embodiment 1. For the solid electrolyte 11, oxides containing barium and cerium, for example, barium-cerium oxides can be used, which is the same as the hydrogen sensor 10 in Embodiment 1.

The first electrode 21 is made of a material being capable of preventing oxygen from being ionized. More specifically, a metal containing at least one selected from the group consisting of aluminum, copper, and nickel can be used, and for example, a pure metal of aluminum, copper or nickel can be used. In this case, the surface of the electrode is oxidized by natural oxidation. For the first electrode 21, other than these metals, a mixture or an alloy containing Pd or Au can be used. For the second electrode 22, a metal containing at least one selected from the group consisting of platinum, gold, silver, palladium, and ruthenium can be used, and for example, a pure metal of platinum, gold, silver, palladium or ruthenium can be used. The first electrode 21 and the second electrode 22 can be formed by firing a metal paste, physical methods such as sputtering, or CVD (chemical vapor deposition method).

In the hydrogen sensor 20 of this embodiment, when a constant voltage is applied between the first electrode 21 as the cathode and the second electrode 22 as the anode, the hydrogen contained in a gas to be measured is dissociated in the second electrode 22, becomes protons, is conducted in the solid electrolyte 11, becomes hydrogen or water in the first electrode 21, and is released. On the other hand, the oxygen contained in the gas to be measured is degraded in the first electrode 21, becomes oxide ions, is conducted in the solid electrolyte 11, becomes hydrogen or water in the second electrode 22, and is released. Thus, charges move in the solid electrolyte 11 in the form of protons and oxide ions, so that a current flows. See FIG. 5B.

In this case, the first electrode 21 is made of a material being capable of preventing oxygen from being ionized, so that the oxygen is not ionized in the first electrode 21, and a current stemming from oxide ions does not substantially flow. Therefore, in the hydrogen sensor 20, the influence of hydrogen that varies the current value by being combined with oxygen in the first electrode 21 is reduced, so that a high concentration of hydrogen contained in the air can be detected more selectively.

Hereinafter, the results of measuring hydrogen concentrations of a gas to be measured with the hydrogen sensor 20 of this embodiment will be described. Herein, sintered $BaZr_{0.4}Ce_{0.4}In_{0.2}O_{3-\alpha}$ and sintered $BaZr_{0.6}Ce_{0.2}Gd_{0.2}O_{3-\alpha}$ were used for the solid electrolyte 11. The size of the solid electrolyte 11 was 10 mm square and 0.5 mm in thickness. The first electrode 21 was formed of a mixture of aluminum and gold, and the second electrode 22 was formed by firing a platinum paste.

As a gas to be measured, a mixed gas of nitrogen and oxygen (oxygen: 20 vol %) was used that was flowing at 1 liter/min and to which 0 to 10 vol % of hydrogen was added at 1 liter/min.

Figure 6:
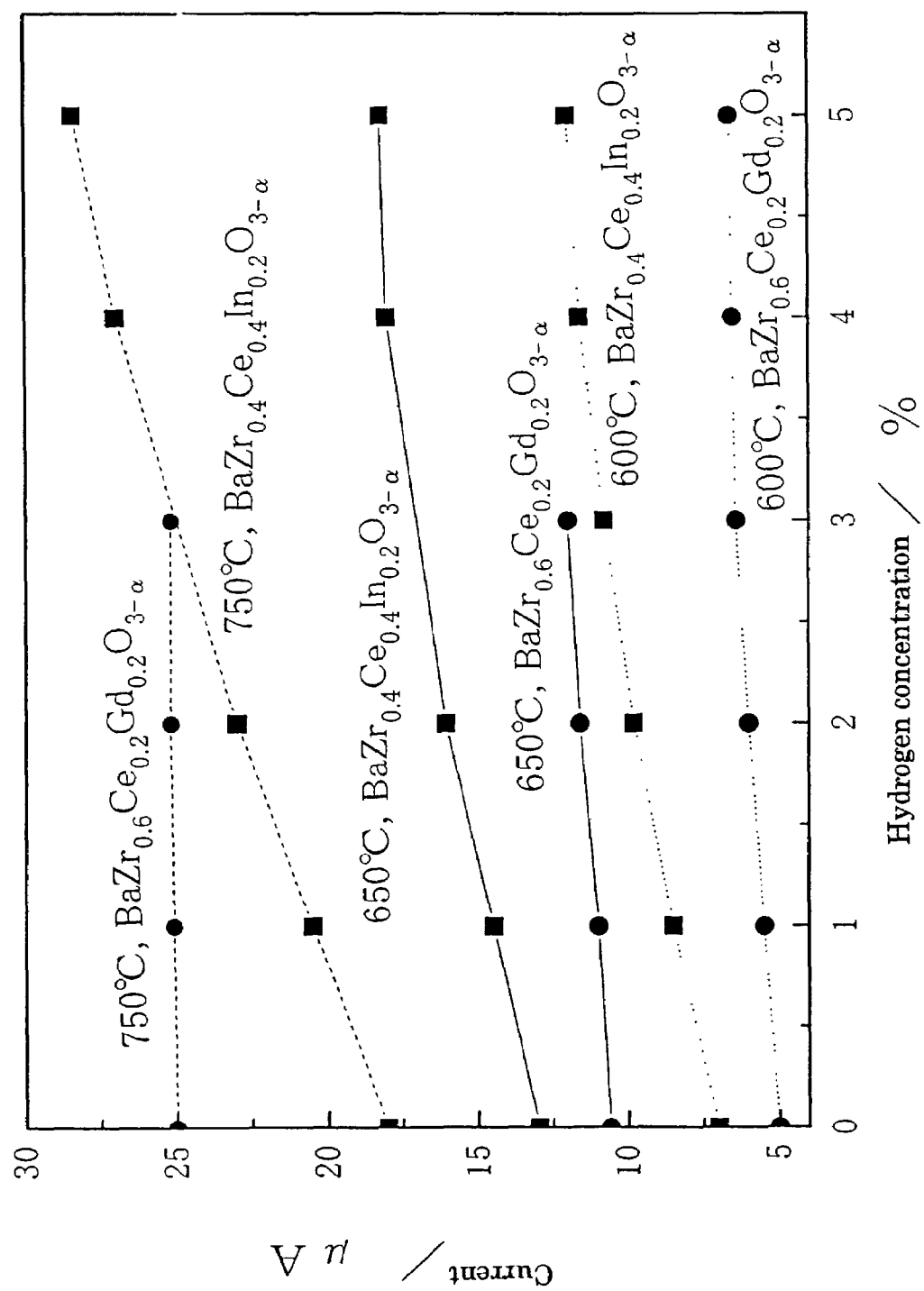
FIG. 6 is a graph showing the relationship between the hydrogen concentration and the current value in the hydrogen sensor of Embodiment 2.

FIG. 6 shows the relationship between the value of the current flowing between the first electrode 21 and the second electrode 22 of the hydrogen sensor 20 and the hydrogen concentration of the gas to be measured. In this embodiment, the solid electrolyte 11 was heated by the heater 14 such that the temperature of the sensor was varied for measurement (the temperatures shown in the graph of FIG. 6 are the temperatures of the sensor at the time of detection of the hydrogen concentrations).

As seen from FIG. 6, hydrogen concentrations in a high concentration region of 0 to 5 vol % were detected stably in the air containing about 20 vol % of oxygen when the sensor temperature was 600 to 750° C. As for the responsiveness, the time until the current value reaches 90% of the final current value was about 10 seconds, which is a good responsiveness.

Furthermore, in this embodiment, in order to investigate the influence of the mixture of other types of gases, 2 vol % each of methane, ethane, propane, butane, carbon monoxide, nitrogen monoxide, carbon dioxide, and water vapor saturated at room temperature were added to the gas to be measured, and an increase or a decrease of the current value was observed. Then, at an atmospheric temperature of 600° C. or less, there was substantially no variation in the current value, and the current values measured were very stable.

The hydrogen sensor 20 of this embodiment can detect stably and easily hydrogen concentrations in a high concentration region of 0 to 5 vol % in the air in the presence of oxygen with excellent responsiveness and hydrogen selectivity. Furthermore, the hydrogen sensor 20 is inexpensive because of its simple structure, and has high reliability.

Embodiment 3

Figure 7A:
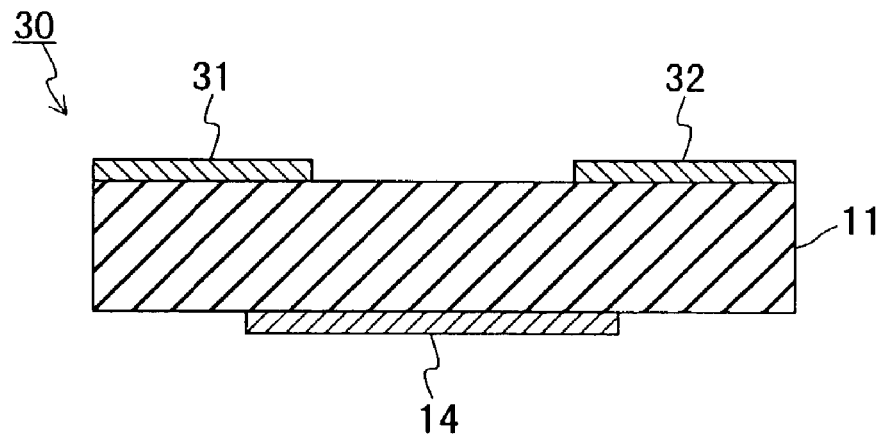
FIG. 7A is a cross-sectional view showing the structure of a hydrogen sensor of Embodiment 3.
Figure 7B:
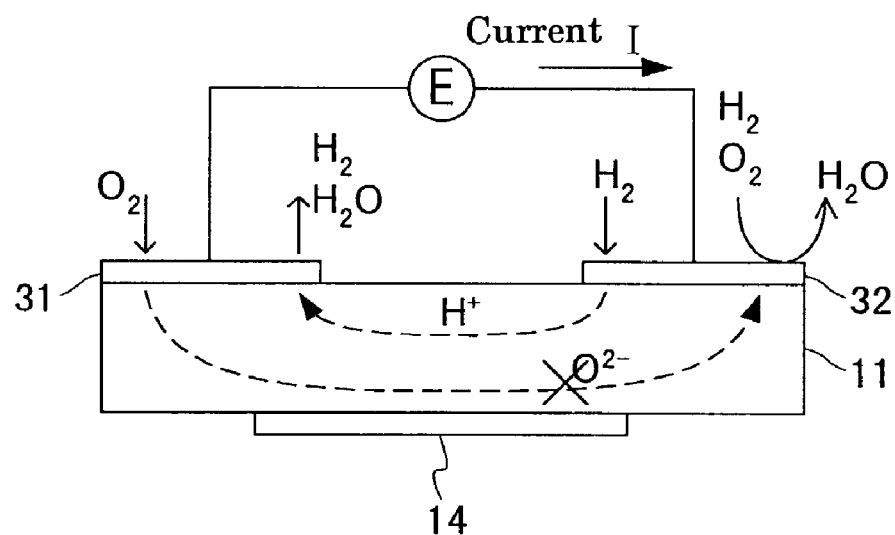
FIG. 7B is a schematic view showing the operation of the hydrogen sensor of Embodiment 3.

FIG. 7A shows a cross-sectional view of the structure of a hydrogen sensor 30 of this embodiment, and FIG. 7B is a schematic view showing the operation thereof. A solid electrolyte 11 is made of an ion conductor that conducts protons ($H^+$) and oxide ions ($O^{2-}$). A first electrode 31 and a second electrode 32 are formed on the surface of the solid electrolyte 11 to conduct ions in the solid electrolyte 11, and a heater 14 for heating the solid electrolyte 11 is provided on the lower surface thereof. The heater 14 can be made of sintered platinum that has been patterned, for example.

The hydrogen sensor 30 is a so-called electromotive force type sensor, and the electromotive force between the first electrode 31 and the second electrode 32 is measured to detect the hydrogen concentration of a gas to be measured. For the solid electrolyte 11, oxides containing barium and cerium, for example, barium-cerium oxides can be used, which is the same as the hydrogen sensors in Embodiments 1 and 2.

The first electrode 31 is made of a material being capable of preventing oxygen from being ionized. More specifically, a metal containing at least one selected from the group consisting of aluminum, copper, and nickel can be used, and for example, a pure metal of aluminum, copper or nickel can be used. In this case, the surface of the electrode is oxidized by natural oxidation. For the first electrode 31, other than these metals, a mixture or an alloy containing Pd or Au can be used. The second electrode 32 is made of a material having a catalytic effect with respect to an oxidation reaction of hydrogen. More specifically, a metal containing at least one selected from the group consisting of platinum, gold, silver, palladium, and ruthenium can be used, and for example, a pure metal of platinum, gold, silver, palladium or ruthenium can be used. The first electrode 31 and the second electrode 32 can be formed by firing a metal paste, physical methods such as sputtering, or CVD (chemical vapor deposition method).

In the hydrogen sensor 30 of this embodiment, the first electrode 31 is made of a material being capable of preventing oxygen from being ionized, so that hydrogen reacts with ambient oxygen so as to be formed into water on the first electrode 31. On the other hand, the second electrode 32 has a catalytic effect with respect to an oxidation reaction of hydrogen, so that a reaction between hydrogen and oxygen hardly occurs and water is produced in only a small amount. Therefore, protons are conducted from the electrode having a high concentration of water vapor to the electrode having a low concentration of water vapor between the first electrode 31 and the second electrode 32, so that electromotive force caused by the difference in the concentration of the water vapor occurs. See FIG. 7B. In the hydrogen sensor 30 of this embodiment, the hydrogen concentration of a gas to be measured can be detected by using this principle to measure the electromotive force between the first electrode 31 and the second electrode 32.

Hereinafter, the results of measuring hydrogen concentrations of a gas to be measured with the hydrogen sensor 30 of this embodiment will be described. Herein, sintered $BaZr_{0.4}Ce_{0.4}In_{0.2}O_{3-\alpha}$, and sintered $BaZr_{0.6}Ce_{0.2}Gd_{0.2}O_{3-\alpha}$ were used for the solid electrolyte 11. The size of the solid electrolyte 11 was 10 mm square and 0.5 mm in thickness. The first electrode 31 was formed of a mixture of aluminum and gold, and the second electrode 32 was formed by firing a platinum paste.

Figure 8:
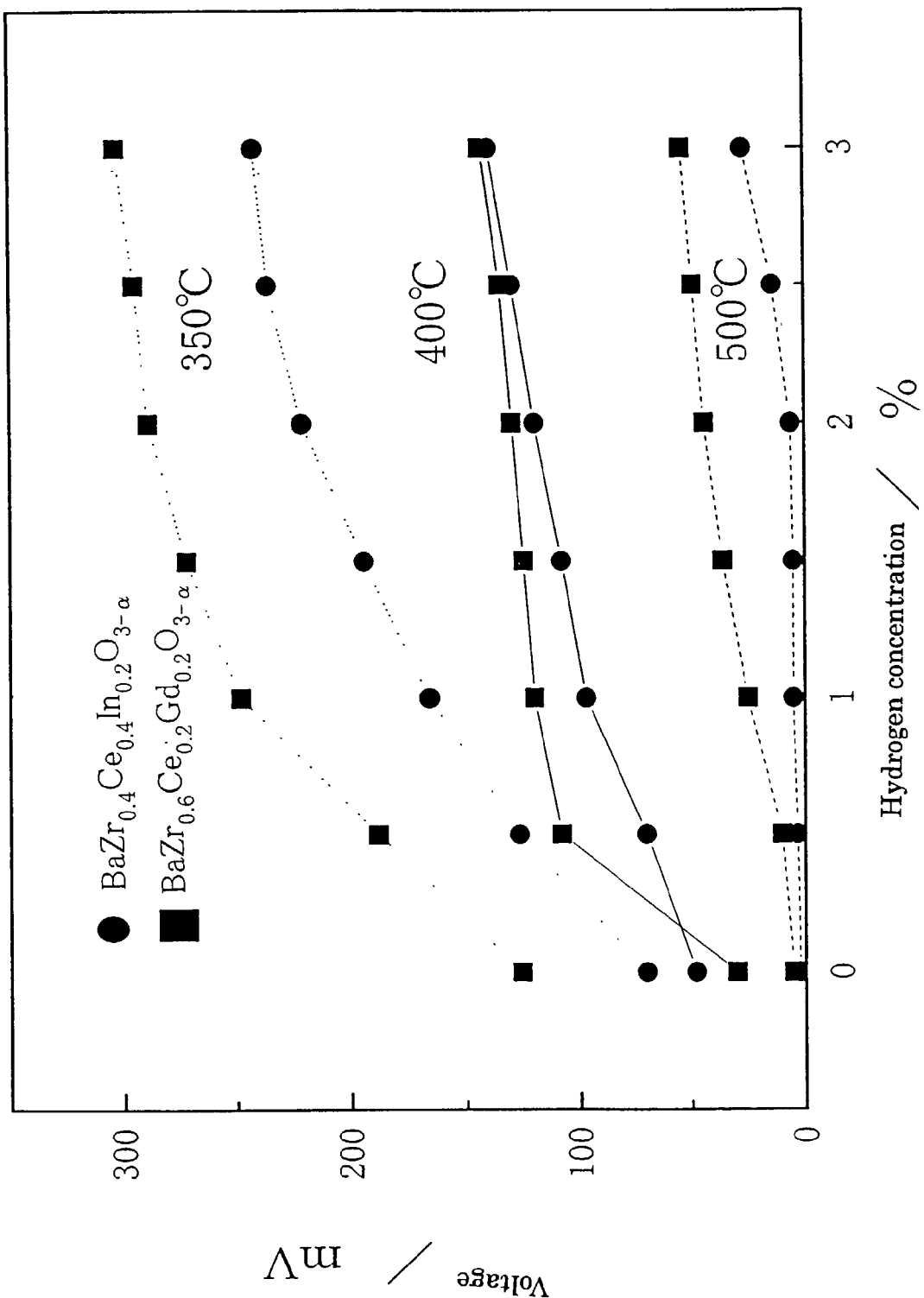
FIG. 8 is a graph showing the relationship between the hydrogen concentration and the current value in the hydrogen sensor of Embodiment 3.

As a gas to be measured, a mixed gas of nitrogen and oxygen (oxygen: 20 vol %) was used that was flowing at 1 liter/min and to which 0 to 6 vol % of hydrogen was added at 1 liter/min. FIG. 8 shows the relationship between the value of the current flowing between the first electrode 31 and the second electrode 32 of the hydrogen sensor 30 and the hydrogen concentration of the gas to be measured. In this embodiment, the solid electrolyte 11 was heated by the heater 14 such that the temperature of the sensor was varied for measurement (the temperatures shown in the graph of FIG. 8 are the temperatures of the sensor at the time of detection of the hydrogen concentrations).

As seen from FIG. 8, hydrogen concentrations in a high concentration region of 0 to 3 vol % were detected in the air containing about 20 vol % of oxygen when the sensor temperature was 350 to 500° C. As for the responsiveness, the time until the current value reaches 90% of the final current value was about 10 seconds, which is a good responsiveness. At comparatively low temperatures of 300 to 350° C. the hydrogen concentration also was detected stably.

Furthermore, in this embodiment, in order to investigate the influence of the mixture of other types of gases, 2 vol % each of methane, ethane, propane, butane, carbon monoxide, nitrogen monoxide, carbon dioxide, and water vapor saturated at room temperature were added to the gas to be measured, and an increase or a decrease of the current value was observed. Then, at an atmospheric temperature of 500° C. or less, there was substantially no variation in the current value, and the current values measured were very stable.

The hydrogen sensor 30 of this embodiment can detect stably and easily hydrogen concentrations in a high concentration region of 0 to 3 vol % in the air in the presence of oxygen, also at comparatively low temperatures, with excellent responsiveness and hydrogen selectivity. Furthermore, the hydrogen sensor 30 is inexpensive because of its simple structure, and has high reliability.

Embodiment 4

Figure 9A:
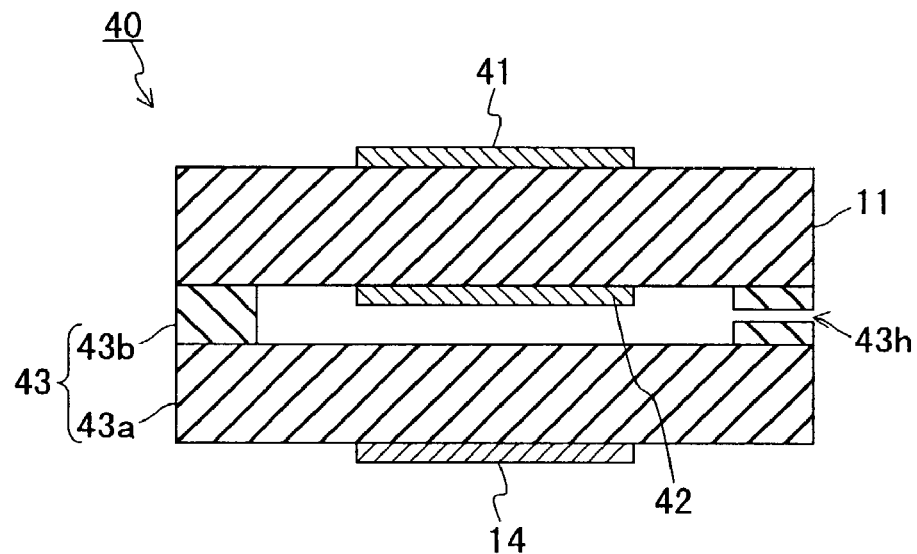
FIG. 9A is a cross-sectional view showing the structure of a hydrogen sensor of Embodiment 4.
Figure 9B:
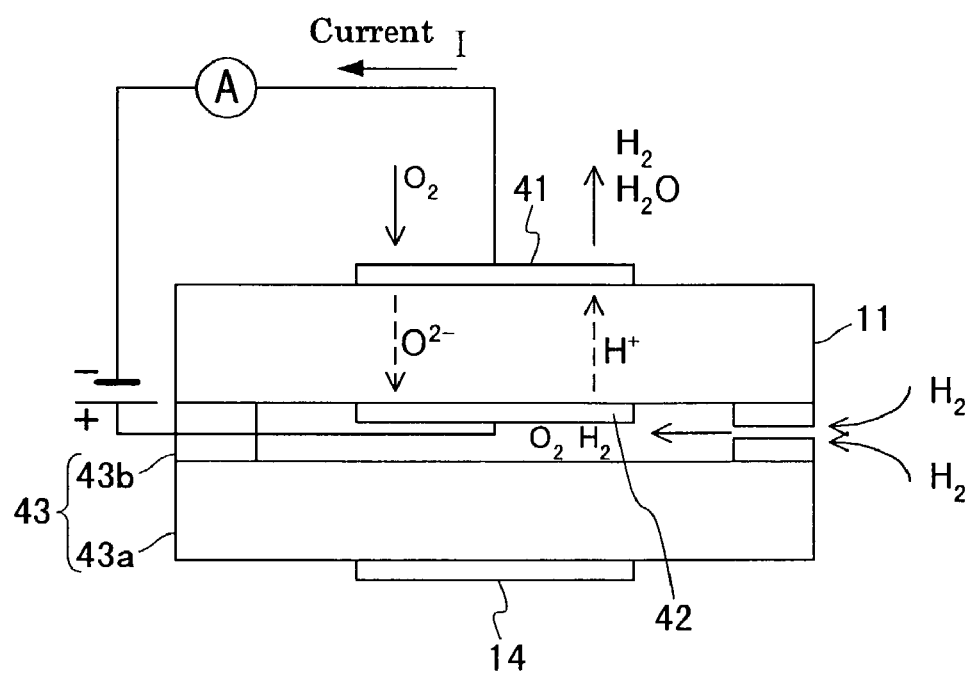
FIG. 9B is a schematic view showing the operation of the hydrogen sensor of Embodiment 4.

FIG. 9A shows a cross-sectional view of the structure of a hydrogen sensor 40 of this embodiment, and FIG. 9B is a schematic view showing the operation thereof. A solid electrolyte 11 is made of an ion conductor that conducts protons ($H^+$) and oxide ions ($O^{2-}$). A first electrode 41 and a second electrode 42 are opposed to each other on the upper and lower surfaces of the solid electrolyte 11 to conduct ions in the solid electrolyte 11. Controlling means 43 for restricting the amount of the hydrogen that reaches the second electrode 42 includes a forsterite substrate 43a and a glass 43b, which are formed so as to cover the second electrode 42. A through-hole 43h is formed in the glass 43b, and a gas to be measured containing hydrogen is introduced from this hole to the second electrode 42. The configuration of the controlling means 43 is not limited thereto, and any other configurations can be used, as long as they can restrict the amount of the hydrogen that reaches the second electrode 42. A heater 14 for heating the solid electrolyte 11 is provided on the lower surface of the glass 43b. The heater 14 can be made of sintered platinum that has been patterned, for example.

The hydrogen sensor 40 is a so-called limiting current type sensor. In this sensor, a constant voltage is applied between the first electrode 41 and the second electrode 42 so that a current generated by the conduction of oxide ions flows steadily between the first electrode 41 and the second electrode 42. In this case, the controlling means 43 restricts hydrogen from passing through the through-hole 43h, and the amount of that hydrogen and the amount of the hydrogen that passes through the solid electrolyte 11 and is released from the second electrode 42 reaches an equilibrium. The amount of the hydrogen at this equilibrium is substantially proportional to the hydrogen concentration of the gas to be measured. The limiting current flowing between the first electrode 42 and the second electrode 42 is substantially proportional to the amount of the hydrogen at the equilibrium. Therefore, the hydrogen concentration of the gas to be measured can be detected precisely by measuring the limiting current.

For the solid electrolyte 11, oxides containing barium and cerium, for example, barium-cerium oxides can be used, which is the same as the hydrogen sensors in Embodiments 1 to 3. The first electrode 42 and the second electrode 42 are made of a material having a catalytic effect with respect to an oxidation reaction of hydrogen and are made of the same material. More specifically, a metal containing at least one selected from the group consisting of platinum, gold, silver, palladium, and ruthenium can be used, and for example, a pure metal of platinum, gold, silver, palladium or ruthenium can be used. The first electrode 42 and the second electrode 42 can be formed by firing a metal paste, physical methods such as sputtering, or CVD (chemical vapor deposition method).

In the hydrogen sensor 40 of this embodiment, when a constant voltage is applied between the first electrode 42 as the cathode and the second electrode 42 as the anode, a current flows through the solid electrolyte 11 in the form of protons and oxide ions. More specifically, the hydrogen contained in a gas to be measured is dissociated in the second electrode 42, becomes protons, is conducted in the solid electrolyte 11, becomes hydrogen or water in the first electrode 41, and is released. On the other hand, the oxygen contained in the gas to be measured is degraded in the first electrode 41, becomes oxide ions, is conducted in the solid electrolyte 11, becomes hydrogen or water in the second electrode 42, and is released. See FIG. 9B.

Hereinafter, the results of measuring hydrogen concentrations of a gas to be measured with the hydrogen sensor 40 of this embodiment will be described. Herein, sintered $BaZr_{0.56}Ce_{0.24}In_{0.2}O_{3-\alpha}$ was used for the solid electrolyte 11. The size of the solid electrolyte 11 was 10 mm square and 0.5 mm in thickness. The first electrode 42 and the second electrode 42 were formed by firing a platinum paste.

Figure 10:
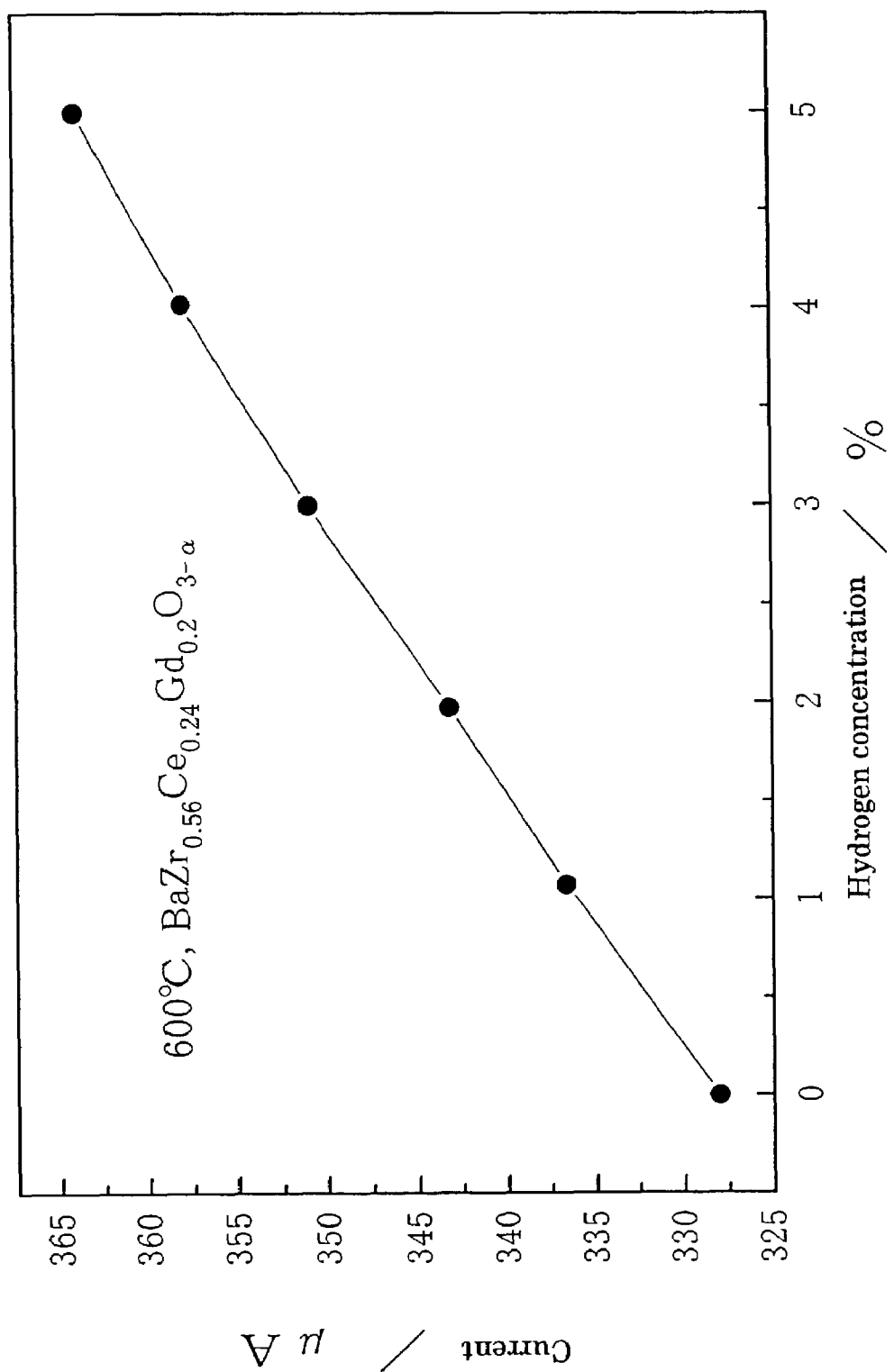
FIG. 10 is a graph showing the relationship between the hydrogen concentration and the current value in the hydrogen sensor of Embodiment 4.

As a gas to be measured, a mixed gas of nitrogen and oxygen (oxygen: 20 vol %) was used that was flowing at 1 liter/min and to which 0 to 10 vol % of hydrogen was added at 1 liter/min. FIG. 10 shows the relationship between the value of the current flowing between the first electrode 42 and the second electrode 42 of the hydrogen sensor 40 and the hydrogen concentration of the gas to be measured. In this embodiment, the solid electrolyte 11 was heated by the heater 14 such that the temperature of the sensor was 600° C. for measurement (the temperature shown in the graph of FIG. 10 is the temperature of the sensor at the time of detection of the hydrogen concentrations).

As seen from FIG. 10, hydrogen concentrations in a high concentration region of 0 to 5 vol % were detected in the air containing about 20 vol % of oxygen. Since the limiting current was detected, the gradient of the current with respect to the hydrogen concentration was increased, and the detection precision of the hydrogen concentration was improved. As for the responsiveness, the time until the current value reached 90% of the final current value was about 2 seconds, which is a very good responsiveness.

Furthermore, in this embodiment, in order to investigate the influence of the mixture of other types of gases, 2 vol % each of methane, ethane, propane, butane, carbon monoxide, nitrogen monoxide, carbon dioxide, and water vapor saturated at room temperature were added to the gas to be measured, and an increase or a decrease of the current value was observed. Then, at an atmospheric temperature of 600° C. or less, there was substantially no variation in the current value, and the current values measured were very stable.

The hydrogen sensor 40 of this embodiment can detect stably and easily hydrogen concentrations in a high concentration region of 0 to 5 vol % in the air in the presence of oxygen with excellent responsiveness and hydrogen selectivity. Furthermore, the hydrogen sensor 40 is inexpensive because of its simple structure, and has high reliability.

Embodiment 5

Figure 11A:
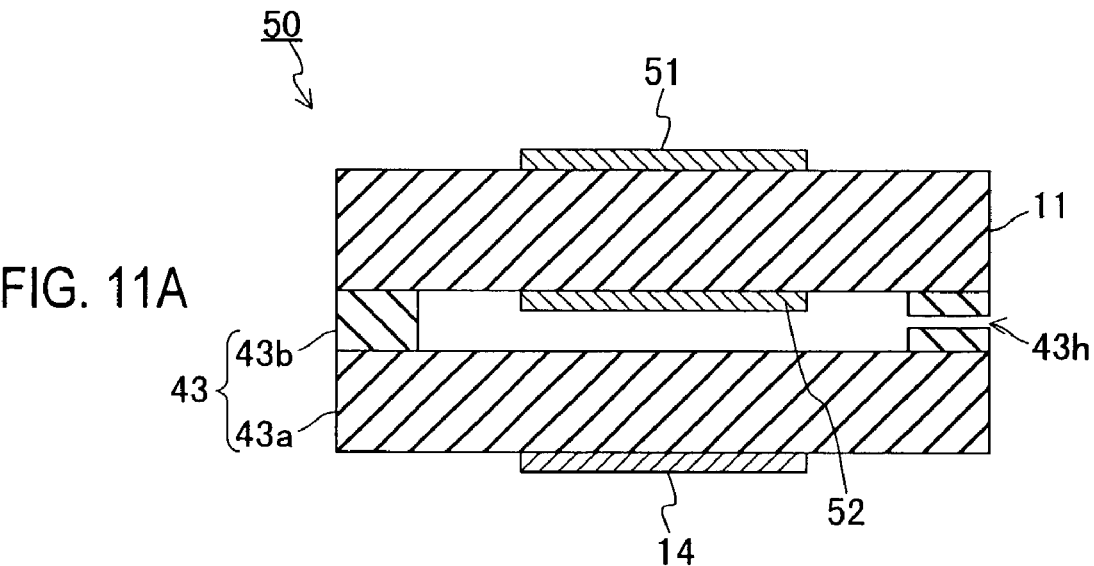
FIG. 11A is a cross-sectional view showing the structure of a hydrogen sensor of Embodiment 5.
Figure 11B:
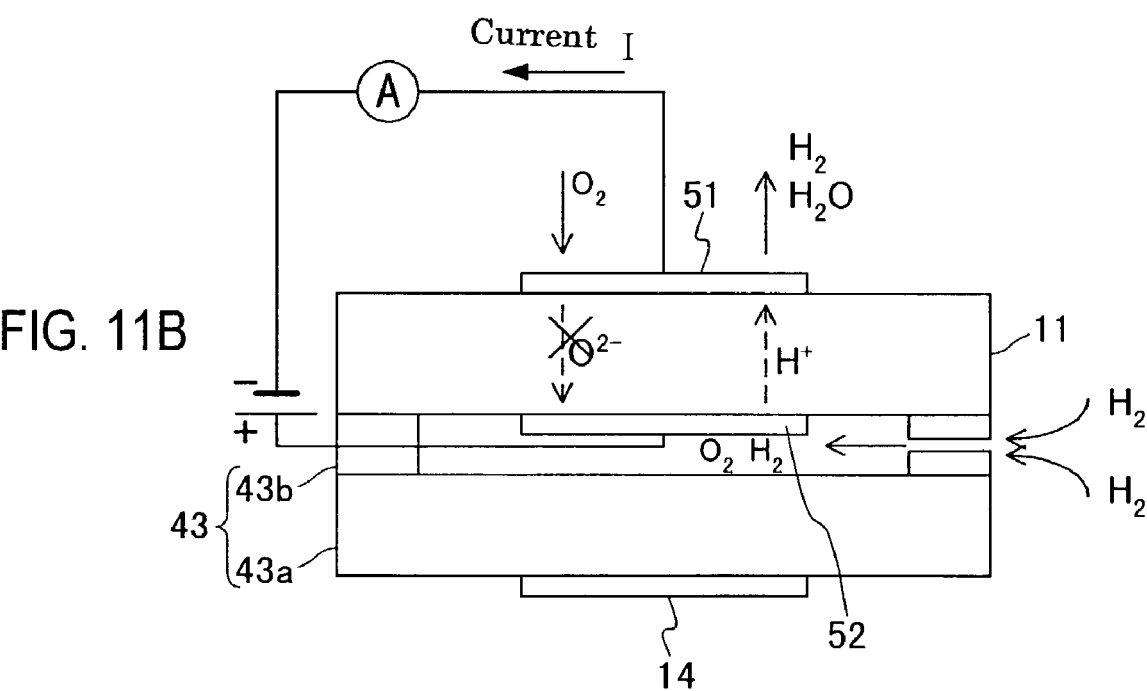
FIG. 11B is a schematic view showing the operation of the hydrogen sensor of Embodiment 5.

FIG. 11A shows a cross-sectional view of the structure of a hydrogen sensor 50 of this embodiment, and FIG. 11B is a schematic view showing the operation thereof. A solid electrolyte 11 is made of an ion conductor that conducts protons ($H^+$) and oxide ions ($O^{2-}$). A first electrode 51 and a second electrode 52 are opposed to each other on the upper and lower surfaces of the solid electrolyte 11 to conduct ions in the solid electrolyte 11. Controlling means 43 for restricting the amount of the hydrogen that reaches the second electrode 52 includes a forsterite substrate 43a and a glass 43b, which are formed so as to cover the second electrode 52. A through-hole 43h is formed in the glass 43b, and a gas to be measured containing hydrogen is introduced from this hole to the second electrode 52. The configuration of the controlling means 43 is not limited thereto, and any other configurations can be used, as long as they can restrict the amount of the hydrogen that reaches the second electrode 52. A heater 14 for heating the solid electrolyte 11 is provided on the lower surface of the glass 43b. The heater 14 can be made of sintered platinum that has been patterned, for example.

The hydrogen sensor 50 is a so-called limiting current type sensor like the hydrogen sensor of Embodiment 4. For the solid electrolyte 11, oxides containing barium and cerium, for example, barium-cerium oxides can be used, which is the same as the hydrogen sensors in Embodiments 1 to 4. At least one of the first electrode 51 and the second electrode 52 is made of a material being capable of preventing oxygen from being ionized. More specifically, a metal containing at least one selected from the group consisting of aluminum, copper, and nickel can be used, and for example, a pure metal of aluminum, copper or nickel can be used. In this case, the surface of the electrode is oxidized by natural oxidation. For the first electrode 51, other than these metals, a mixture or an alloy containing Pd or Au can be used.

In this embodiment, a material being capable of preventing oxygen from being ionized is used for the first electrode 51, but it can be used for the second electrode 52. When the material being capable of preventing oxygen from being ionized is used for the first electrode 51, the second electrode 52 can be formed of a material having a high conductivity. For example, it is preferable to form the second electrode 52 of a material having a catalytic effect with respect to an oxidation reaction of hydrogen. More specifically, a metal containing at least one selected from the group consisting of platinum, gold, silver, palladium, and ruthenium can be used, and for example, a pure metal of platinum, gold, silver, palladium or ruthenium can be used. The first electrode 51 and the second electrode 52 can be formed by firing a metal paste, physical methods such as sputtering, or CVD (chemical vapor deposition method).

In the hydrogen sensor 50 of this embodiment, when a constant voltage is applied between the first electrode 51 as the cathode and the second electrode 52 as the anode, a current flows the solid electrolyte 11 in the form of protons and oxide ions. More specifically, the hydrogen contained in a gas to be measured is dissociated in the second electrode 52, becomes protons, is conducted in the solid electrolyte 11, becomes hydrogen or water in the first electrode 51, and is released. On the other hand, the oxygen contained in the gas to be measured is degraded in the first electrode 51, becomes oxide ions, is conducted in the solid electrolyte 11, becomes hydrogen or water in the second electrode 52, and is released, See FIG. 11B.

In the hydrogen sensor 50, the first electrode 51 is capable of preventing oxygen from being ionized, so that the oxygen is not ionized in the first electrode 51, and oxide ions do not substantially flow. Therefore, in the hydrogen sensor 50, the influence of hydrogen that varies the current value by being combined with oxygen in the first electrode 51 is reduced, so that hydrogen contained in the air can be detected more selectively.

Hereinafter, the results of measuring hydrogen concentrations of a gas to be measured with the hydrogen sensor 50 of this embodiment will be described. Herein, sintered $BaZr_{0.2}Ce_{0.6}In_{0.2}O_{3-\alpha}$ was used for the solid electrolyte 11. The size of the solid electrolyte 11 was 10 mm square and 0.5 mm in thickness. The first electrode 51 was formed of a mixture of aluminum and gold, and the second electrode 52 was formed of platinum.

Figure 12:
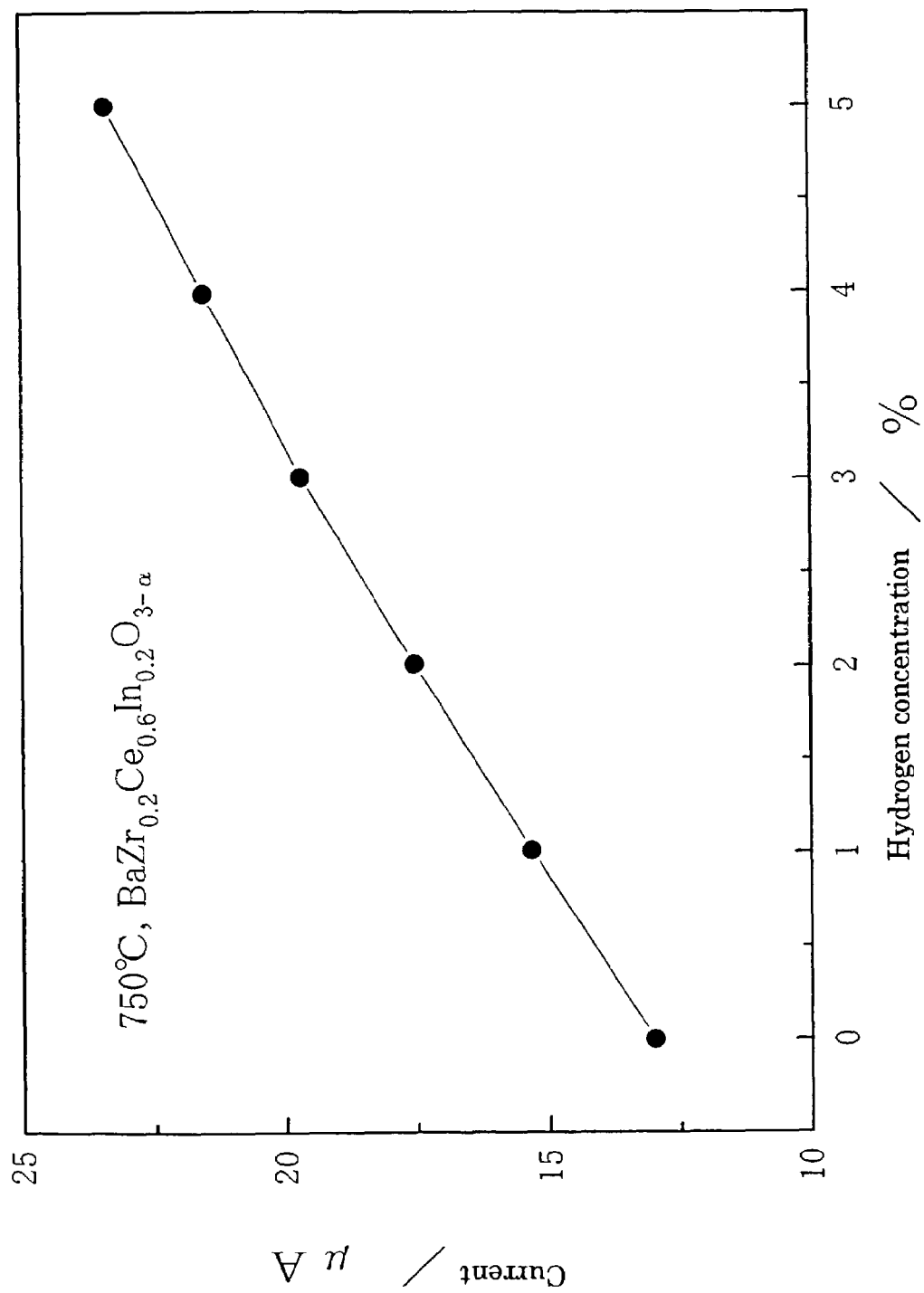
FIG. 12 is a graph showing the relationship between the hydrogen concentration and the current value in the hydrogen sensor of Embodiment 5.

As a gas to be measured, a mixed gas of nitrogen and oxygen (oxygen: 20 vol %) was used that was flowing at 1 liter/min and to which 0 to 10 vol % of hydrogen was added at 1 liter/min. FIG.12 shows the relationship between the value of the current flowing between the first electrode 51 and the second electrode 52 of the hydrogen sensor 50 and the hydrogen concentration of the gas to be measured. In this embodiment, the solid electrolyte 11 was heated by the heater 14 such that the temperature of the sensor was 750° C. for measurement (the temperature shown in the graph of FIG. 12 is the temperature of the sensor at the time of detection of the hydrogen concentrations).

As seen from FIG. 12, hydrogen concentrations in a high concentration region of 0 to 5 vol % were detected in the air containing about 20 vol % of oxygen. Since the limiting current was detected, the gradient of the current with respect to the hydrogen concentration is increased, and the detection precision of the hydrogen concentration was improved. As for the responsiveness, the time until the current value reached 90% of the final current value was about 2 seconds, which is a very good responsiveness.

Furthermore, in this embodiment, in order to investigate the influence of the mixture of other types of gases, 2 vol % each of methane, ethane, propane, butane, carbon monoxide, nitrogen monoxide, carbon dioxide, and water vapor saturated at room temperature were added to the gas to be measured, and an increase or a decrease of the current value was observed. Then, at an atmospheric temperature of 600° C. or less, there was substantially no variation in the current value, and the current values measured were very stable.

The hydrogen sensor 50 of this embodiment can detect stably and easily hydrogen concentrations in a high concentration region of 0 to 5 vol % in the air in the presence of oxygen with excellent responsiveness and hydrogen selectivity. Furthermore, the hydrogen sensor 50 is inexpensive because of its simple structure, and has high reliability.

Embodiment 6

Figure 13:
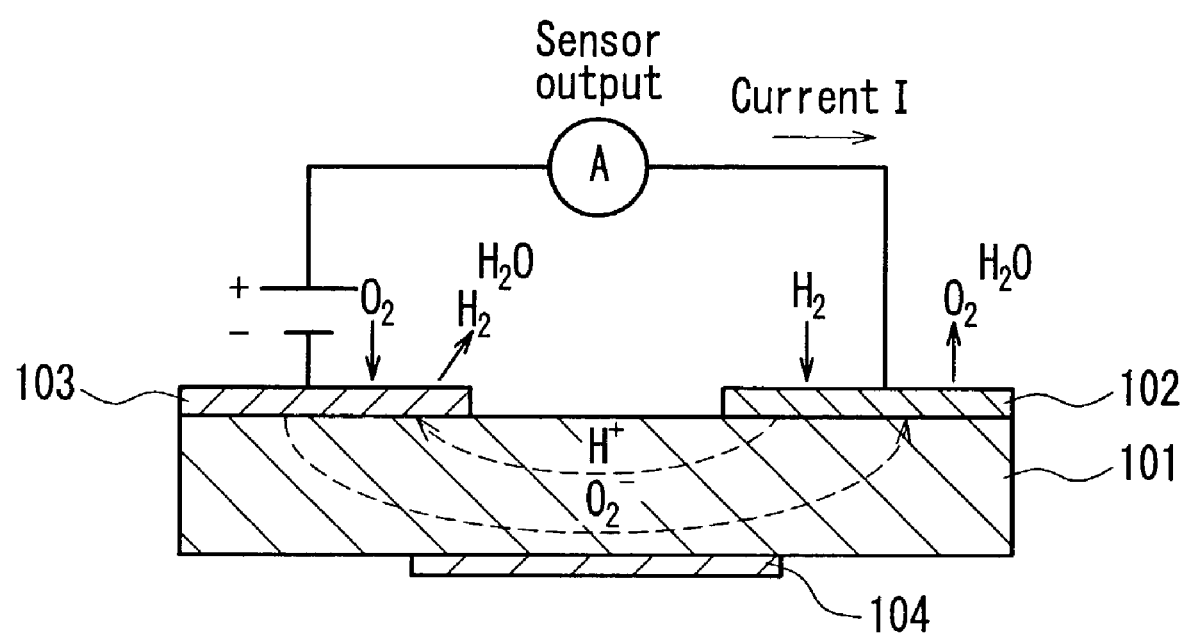
FIG. 13 is a schematic view showing the structure of a hydrogen sensor of Embodiment 6.

FIG. 13 shows a cross-sectional view showing the structure and the operation of a hydrogen sensor of this embodiment. This hydrogen sensor is a so-called a current detection type sensor like the hydrogen sensors 10 and 20 in Embodiments 1 and 2. A solid electrolyte 101 is made of sintered $BaZr_{0.6}Ce_{0.2}Gd_{0.2}O_{3-\alpha}$, which conducts protons ($H^+$) and oxide ions ($O^{2-}$)g. The size thereof is 10 mm square and 0.45 mm in thickness, and the sensor includes an anode electrode 102 made of platinum and a cathode electrode 103 formed of platinum (electrode area is 0.5 $cm^2$). These electrodes are produced by firing a platinum paste. These electrodes have a catalytic effect with respect to an oxidation reaction of hydrogen. A heater 104 for heating the solid electrolyte 101 is provided.

In the hydrogen sensor of this embodiment, a voltage is applied between the anode electrode 102 and the cathode electrode 103, and the voltage was varied as appropriate. The temperature of the heater 104 was set to 400° C., and while the temperature of the sensor was kept 400° C., air and a mixed gas of air and hydrogen were supplied at 1 liter/min. Then, the detection state of the sensor was observed in each case.

Figure 14:
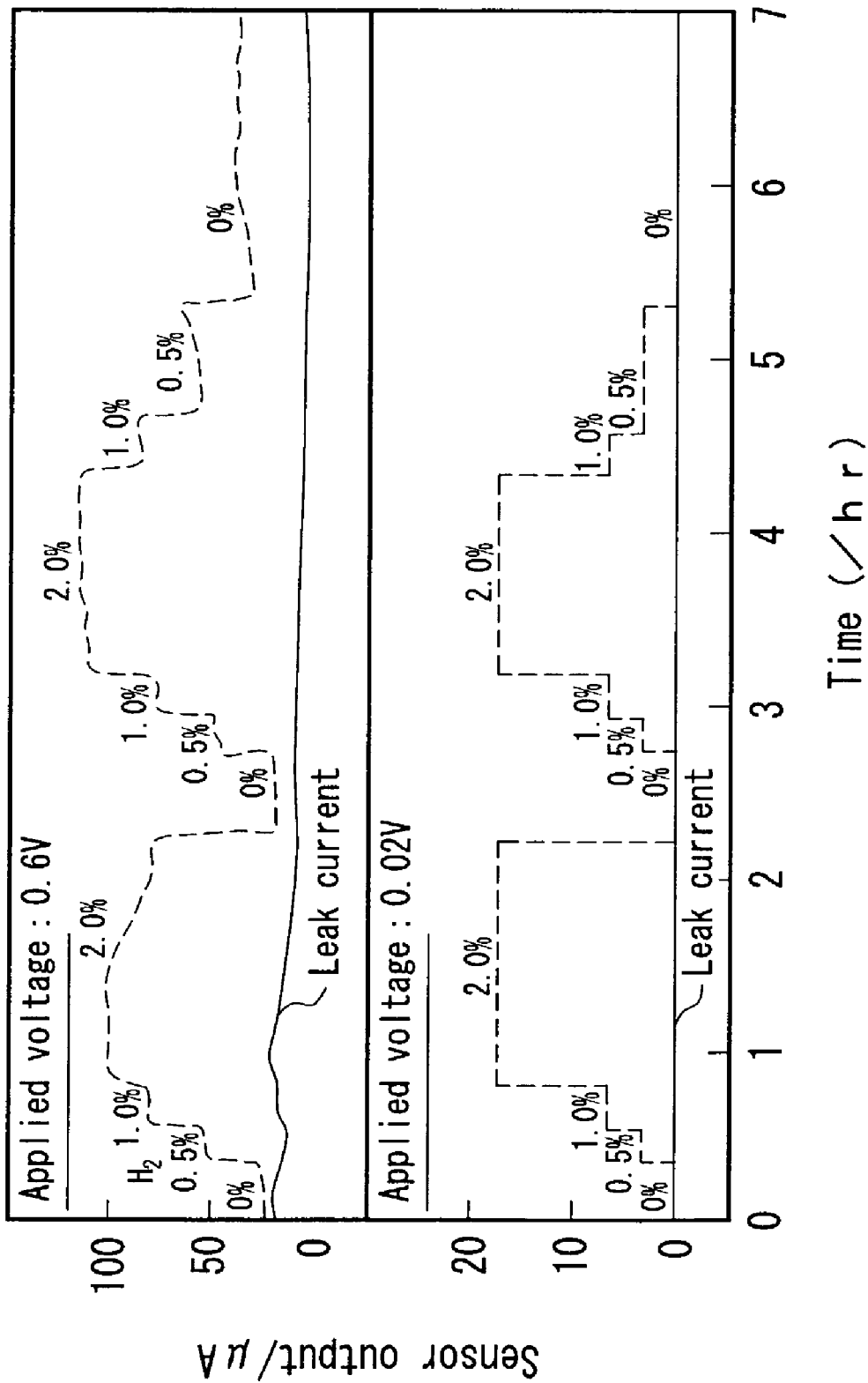
FIG. 14 is a graph showing temporal changes of the sensor output and the leak current in the hydrogen sensor of Embodiment 6.

FIG. 14 shows a graph of temporal changes of sensor outputs when the applied voltage is 0.6V (1.33V/mm) (the parenthesized figure is the electrolytic field intensity, which is a potential gradient per unit thickness of the solid electrolyte 101, which also applies to the following) and 0.02 V (0.044 V/mm) in this embodiment. In the graph of FIG. 14, the broken line indicates the sensor output (µA), and the % representation along the broken line is the amount of added hydrogen (vol %) at the time when each sensor output (µA) was obtained. The solid line indicates the leak current in each applied voltage, that is, a current steadily flowing between the cathode electrode 103 and the anode electrode 102 when hydrogen is not added to the air. Thus, when the applied voltage is 0.02 V and the electrolytic field intensity is 0.044 V/mm, the leak current is very stable at a low value of 0.78±0.01 µA, and the detection precision of the hydrogen concentration is very good, compared with the case where the applied voltage is 0.6 V and the electrolytic field intensity is 1.33 V/mm.

When the applied voltage is 0.02 V, even if 2.0 vol % of hydrogen is added to increase the hydrogen concentration, the leak current is stable at a low value of 18±1 µA, and the detection precision of the hydrogen concentration is still good. As for the responsiveness, the time until the current value reaches 90% of the final current value was about 2 seconds, which is a very good responsiveness.

Although not shown, also when the applied voltage is 0.01 V (0.022 V/mm), 0.04 V (0.089 V/mm), 0.06 V (0.13 V/mm), or 0.1 V (0.22 V/mm), the leak current (µA) is stable at a low value, the sensor output (µA) is at least ten times the leak current (µA), and the detection precision of the hydrogen concentration was good. However, when the applied voltage is increased to 0.6 V (1.33V/mm), 0.8 V (1.78 V/mm), and 1.0 V (2.2 V/mm), the leak current increases so that the detection precision of the hydrogen concentration deteriorates, and the drift amount of the sensor outputs (µA) becomes ±5% or more with respect to 100% of the sensor output (µA) and thus the detection state of the sensor becomes unstable.

The cause of this phenomenon can be explained as follows. In general, when a voltage is applied to a solid electrolyte, primarily oxide ions are conducted in the case of the air. When the applied voltage is increased, a current stemming from oxide ions flows correspondingly in a larger amount. The conductivity (resistivity) of the ions of the solid electrolyte varies, depending on the ambient temperature or the gas concentration in the surroundings. Therefore, when the applied voltage is increased, the current amount that changes depending on the ambient temperature or the gas concentration in the surroundings increases, so that the drift amount of the sensor output (µA) is increased.

According to the hydrogen sensor of this embodiment, when the applied voltage is 0.5V or less, that is, the electrolytic field intensity is 1.11 V/mm or less, preferably 0.22 V/mm or less, the leak current (µA) is stable at a low value and the detection precision of the hydrogen concentration can be increased.

Furthermore, in general, when a high voltage is applied and oxide ions are forced to flow, oxygen locally becomes deficient, which may cause the sensor to deteriorate. However, according to the hydrogen sensor of this embodiment, the applied voltage and the electrolytic field intensity can be suppressed to be low, so that the deterioration of the sensor can be prevented effectively.

In this embodiment, the temperature of the sensor at the time of the detection of the hydrogen concentration is 400° C., but this temperature can be in the range from 200 to 450° C.

Embodiment 7

A hydrogen sensor of this embodiment is a a current detection type sensor, and has the same structure as the hydrogen sensor of Embodiment 6. In this hydrogen sensor, a voltage was applied between the anode electrode 102 and the cathode electrode 103, and the voltage was varied as appropriate. At this time, the temperature of the sensor was changed sequentially, and the detection state of the sensor was observed for each temperature while 0 to 2.0 vol % of hydrogen was added to the air. In this embodiment, a mixed gas of air and hydrogen was supplied at 1 liter/min. Table 1 shows the results.

TABLE 1

| Temperature (° C.) | Voltage for stability (V) | Electrolytic field intensity for stability (V/mm) |
|---|---|---|
| 150 | — | — |
| 200 | 1.0 to 1.4 | 2.22 to 3.11 |
| 250 | 0.02 to 0.8 | 0.044 to 1.78 |
| 300 | 0.02 to 0.5 | 0.044 to 1.11 |
| 350 | 0.02 to 0.5 | 0.044 to 1.11 |
| 400 | 0.02 to 0.4 | 0.044 to 0.89 |
| 450 | 0.02 to 0.1 | 0.044 to 0.22 |

In Table 1, "stability" in "Voltage for stability" and Electrolytic field intensity for stability" means that the leak current is stable at a low value of 5 µA (leak current density; 10 µA/$cm^2$) or less.

As shown in Table 1, according to this embodiment, when the temperature of the sensor at the time of the detection of the hydrogen concentration is 300° C. or more, in the vicinity of 250° C. and in the vicinity of 200° C., the electrolytic field intensity is changed in accordance with each temperature and set to 0.044 to 1.11 V/mm, 0.044 to 1.78 V/mm, and 2.22 to 3.11 V/mm, then the leak current (μA) becomes stable, and the detection precision of the hydrogen concentration can be increased.

Embodiment 8

A hydrogen sensor of this embodiment is a a current detection type sensor, and has the same structure as the hydrogen sensors of Embodiments 6 and 7. In this hydrogen sensor, a voltage in the range from 0.02 to 1.0 V was applied between the anode electrode 102 and the cathode electrode 103, and the voltage was varied as appropriate. Thus, the leak current was varied, the air was supplied at 1 liter/min, and the sensor output characteristics were observed. Table 2 shows the relationship between the leak current density (μA/cm$^2$) [a value obtained by dividing the leak current (μA) by the electrode area (cm$^2$) and the drift amount (%) of the leak current density (μA/cm$^2$) for 24 hours of the measurement.

TABLE 2

| Leak current (μA) | Leak current density (μA/cm$^2$) | Drift amount (%) [for 24 hours of measurement] |
|---|---|---|
| 0.053 | 0.106 | ±0.5% |
| 0.121 | 0.242 | ±1.0% |
| 0.610 | 1.220 | ±1.0% |
| 0.782 | 1.564 | ±1.2% |
| 0.991 | 1.982 | ±4.8% |
| 1.021 | 2.042 | ±5.4% |
| 1.542 | 3.084 | ±6.2% |
| 3.421 | 6.842 | ±15.3% |
| 6.450 | 12.900 | −20.1% |

As shown in Table 2, according to this embodiment, when the leak current density at the time of the detection of the hydrogen concentration is 3 μA/cm$^2$ or less, preferably 2 μA/cm$^2$ or less, then the drift amount of the leak current density can be suppressed to 6.2% or less, so that the detection state of the sensor becomes stable.

The cause of this phenomenon can be explained as follows. In general, when a voltage is applied to a solid electrolyte, primarily oxide ions are conducted in the case of the air. When the leak current, that is, the amount of a current steadily flowing through the solid electrolyte, is increased, a current stemming from oxide ions flows correspondingly in a larger amount. The conductivity (resistivity) of the ions of the solid electrolyte varies, depending on the ambient temperature or the gas concentration in the surroundings. Therefore, when the leak current per unit area of the electrode is increased, the amount of the leak current that changes depending on the ambient temperature or the gas concentration in the surroundings increases, so that the drift amount of the leak current density is increased.

In this embodiment, the temperature of the sensor at the time of the detection of the hydrogen concentration is 350° C., but this temperature can be in the range from 200 to 450° C.

In Embodiments 6 to 8, the thickness of the solid electrolyte is 0.45 mm, but it is preferable that the thickness of the solid electrolyte is as thin as possible, because a small thickness requires only a low voltage to be applied, and the range from 0.20 to 1.00 mm is preferable as a practical range.

In Embodiments 6 to 8, sintered $BaZr_{0.6}Ce_{0.2}Gd_{0.2}O_{3-\alpha}$ is used as the solid electrolyte, but other ion conductors can be used, as long as they are ion conductors such as barium-cerium oxides that conduct protons and oxide ions. For example, the barium-cerium oxides listed illustrated in Embodiments 1 to 5, such as sintered $BaZr_{0.4}Ce_{0.4}In_{0.2}O_{3-\alpha}$, $BaCe_{0.8}Gd_{0.2}O_{3-\alpha}$, $BaZr_{0.4}Ce_{0.4}Gd_{0.2}O_{3-\alpha}$, $BaZr_{0.4}Ce_{0.4}Yb_{0.2}O_{3-\alpha}$, and $BaZr_{0.2}Ce_{0.65}Gd_{0.15}O_{3-\alpha}$ can be used.

Embodiment 9

Figure 15:
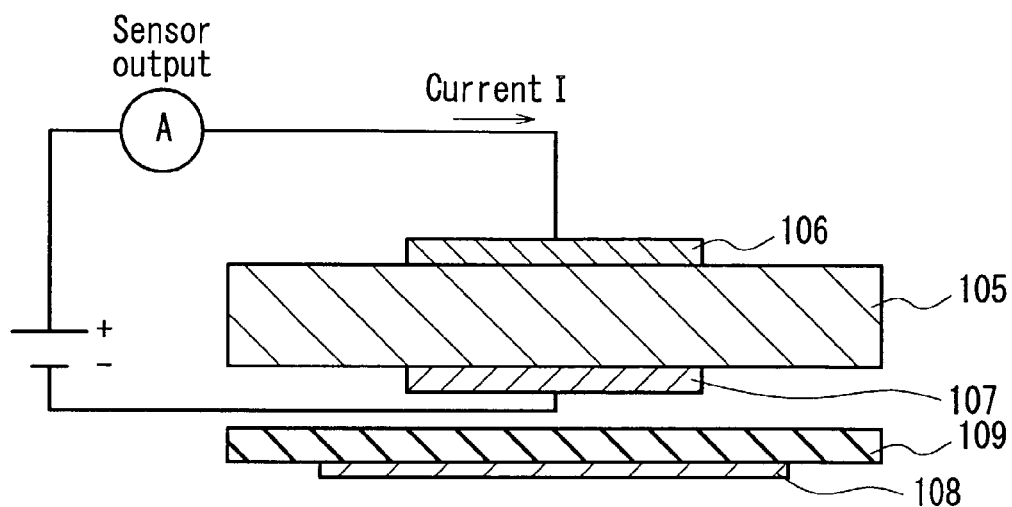
FIG. 15 is a schematic view showing the structure of a solid hydrogen sensor of Embodiment 9.

FIG. 15 is a schematic view showing the structure of a hydrogen sensor of this embodiment. This hydrogen sensor is a so-called constant electrolytic solid type sensor. A solid electrolyte 105 is made of sintered $BaZr_{0.4}Ce_{0.4}In_{0.2}O_{3-\alpha}$, which conducts protons (H$^+$) and oxide ions (O$^{2-}$). The size thereof is 10 mm square and 0.5 mm in thickness, and the sensor includes a platinum anode electrode 106 produced by firing a platinum paste, a heater 108, a heater substrate 109 made of a ceramic, and a platinum cathode electrode 107 produced by firing a platinum paste and provided above the heater 108 by the heater substrate 109 interposed between them.

In the hydrogen sensor of this embodiment, if both the cathode electrode 107 and the anode electrode 106 are made of a material having a large catalytic effect with respect to an oxidation reaction of hydrogen such as platinum, the two electrodes are equipotential so that a current that depends only on the applied potential flows. In this case, when one of the electrodes is heated or cooled, a potential difference is generated by the difference in the temperature between the electrodes. For example, when the cathode electrode 107 is heated to make the catalytic effect with respect to an oxidation reaction of hydrogen faster than that of the anode electrode 106, oxidation reaction is activated on the side of the cathode electrode 107. Then, protons flow through the solid electrolyte 105 from the anode electrode 106 to the cathode electrode 107, and a current flows from the cathode electrode 107 to the anode electrode 106 in an external circuit. In other words, when the air to which hydrogen is added is measured, the amount of a current flowing from the positive electrode to the negative electrode of the battery increases in the external circuit. Utilizing this principle, the detection precision of the hydrogen concentration can be increased.

In this hydrogen sensor, a voltage of 0.02 V was applied between the anode electrode 106 and the cathode electrode 107. The temperature of the heater 108 was set to 400° C., and while the temperature of the sensor was kept at 400° C., air and a mixed gas of air and hydrogen were supplied at 1 liter/min. Then, the detection state of the sensor was observed in each case.

Figure 16:
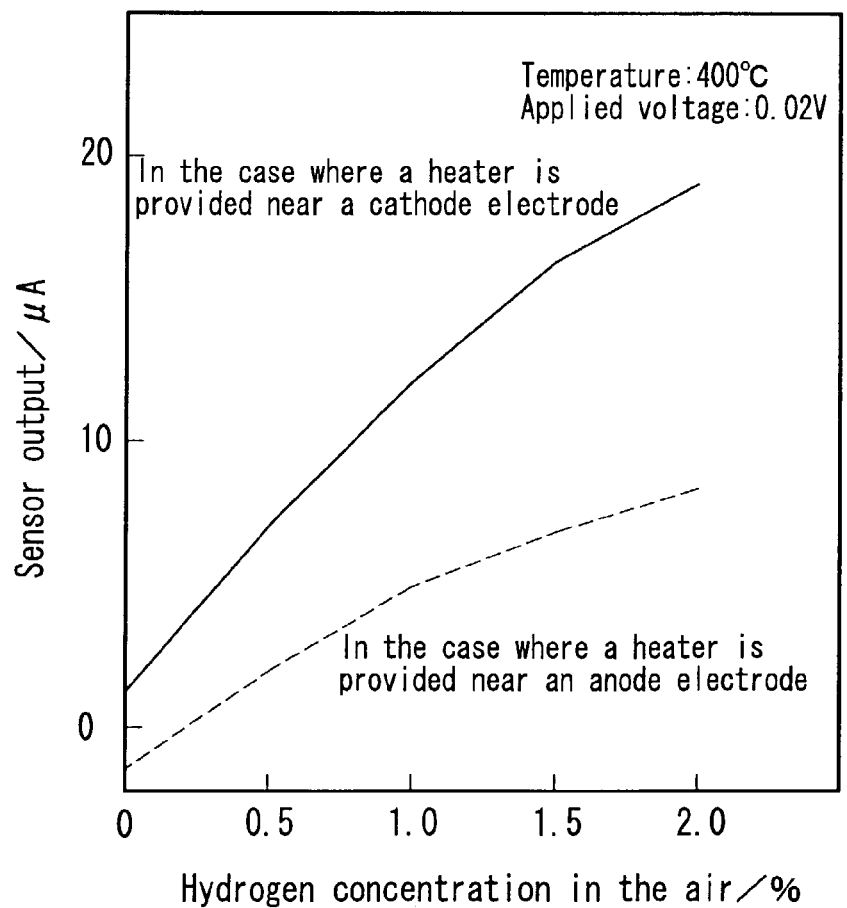
FIG. 16 is a graph showing the relationship between the sensor output and the hydrogen concentration in the air in the hydrogen sensor of Embodiment 9.

FIG. 16 is a graph showing the sensor output characteristics when the heater 108 is provided near the cathode electrode 107 for heating, and when the heater 108 is provided near the anode electrode 106 for heating. In the former case, although the leak current was slightly larger, the leak current density was a low value of 3 μA/cm$^2$ or less, and the detection precision of the hydrogen concentration was good. Also in the case where the temperature of the heater 108 was changed to 200° C. and 300° C., the detection precision of the hydrogen concentration was better when the heater 108 was provided near the cathode electrode 107.

Thus, according to the hydrogen sensor of this embodiment, the leak current density (μA/cm$^2$) can be stable at a low value and the detection precision of the hydrogen concentration can be increased by providing the heater 108 near the cathode electrode 107.

In the hydrogen sensor in this embodiment, the electrodes and the heater are separate members, and are in contact with each other in the vertical direction. However, the electrodes and the heater may be one unit, and may be in contact with in the horizontal direction. Furthermore, the electrodes may be provided not in the vertical direction, but provided on the solid electrolyte side by side in the horizontal direction. If the electrodes are provided on the solid electrolyte in the horizontal direction, the cathode electrode can be provided either on the right or the left, and in this case, the heater may be provided above the cathode electrode.

In the Embodiments, sintered $BaZr_{0.4}Ce_{0.4}In_{0.2}O_{3-\alpha}$ is used as the electrolyte, but other ion conductors can be used, as long as they are ion conductors such as barium-cerium oxides that conduct protons and oxide ions. For example, the barium-cerium oxides listed in Embodiments 1 to 5, such as sintered $BaZr_{0.6}Ce_{0.2}Gd_{0.2}O_{3-\alpha}$, $BaCe_{0.8}Gd_{0.2}O_{3-\alpha}$, $BaZr_{0.4}Ce_{0.4}Gd_{0.2}O_{3-\alpha}$, $BaZr_{0.4}Ce_{0.4}Yb_{0.2}O_{3-\alpha}$, $BaZr_{0.2}Ce_{0.65}Gd_{0.15}O_{3-\alpha}$, or the like can be used.

In Embodiments 6 to 9, the electrode area is 0.5 cm$^2$, but it is preferable that the electrode area is small for compactness of the sensor, whereas it is preferable that it is large for the purpose of increasing the sensor output. Therefore, it is preferable in practice that the electrode area is in the range from 0.01 to 2.0 cm$^2$.

In Embodiments 6 to 9, the electrodes are made of platinum. However, other than that, a metal containing at least one selected from the group consisting of platinum, gold, silver, palladium, and ruthenium can be used, and for example, a pure metal of gold, silver, palladium or ruthenium or alloys of these metals can be used as the material of the electrodes. In Embodiments 6 to 9, the platinum electrodes are produced by firing a platinum paste, but can be formed by physical deposition methods such as sputtering, or CVD (chemical vapor deposition).

Embodiment 10

Figure 17A:
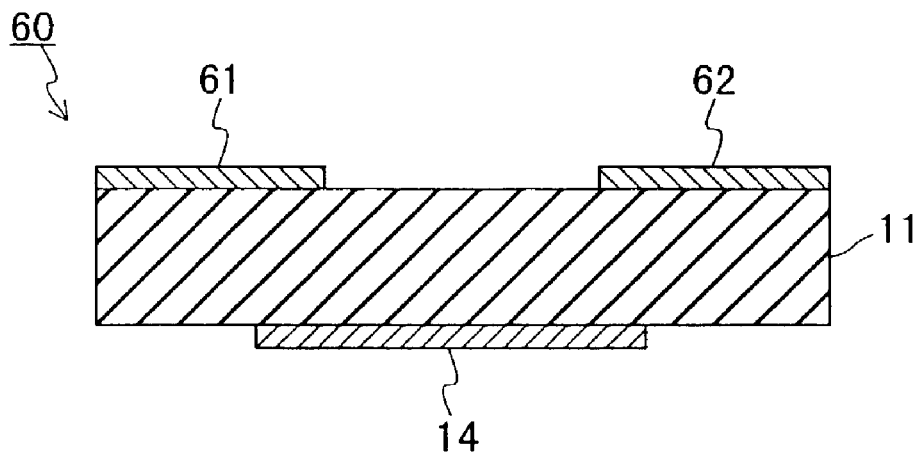
FIG. 17A is a cross-sectional view showing the structure of a hydrogen sensor of Embodiment 10.
Figure 17B:
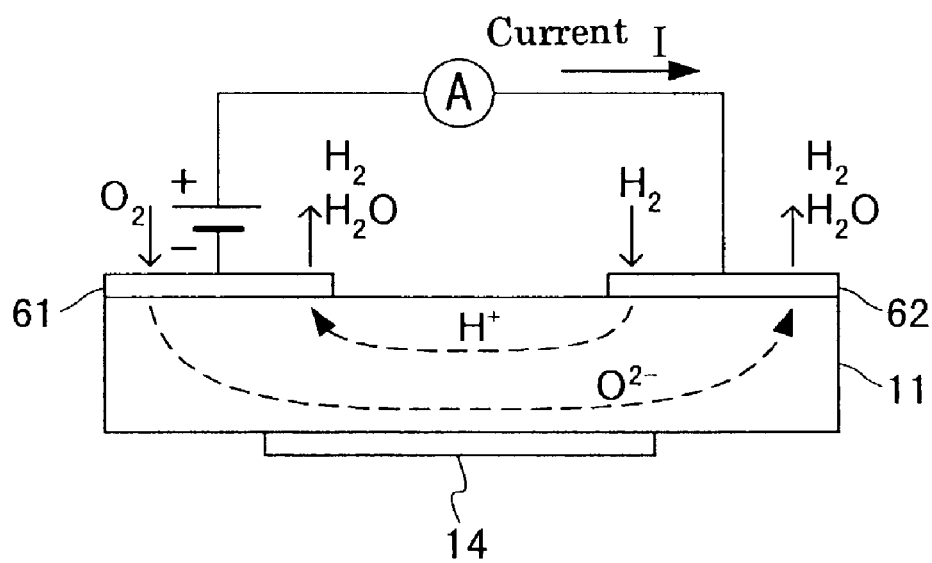
FIG. 17B is a schematic view showing the operation of the hydrogen sensor of Embodiment 10.

FIG. 17A is a schematic view showing the structure of a hydrogen sensor 60 of this embodiment, and FIG. 17B is a schematic view of the operation thereof. A solid electrolyte 11 is made of an ion conductor that conducts protons (H$^+$) and oxide ions (O$^{2-}$). A first electrode 61 and a second electrode 62 are formed on the surface of the solid electrolyte 11 to conduct ions in the solid electrolyte 11, and a heater 14 for heating the solid electrolyte 11 is provided on the lower surface thereof. The heater 14 can be made of sintered platinum that has been patterned, for example. The first electrode 61 and the second electrode 62 are made of platinum having a catalytic effect with respect to an oxidation reaction of hydrogen (electrode area 0.5 cm$^2$). These electrodes are produced by firing a platinum paste.

The hydrogen sensor 60 is a so-called a current detection type sensor like the hydrogen sensors 10 and 20 in Embodiments 1 and 2. For the solid electrolyte 11, oxides containing barium and cerium, for example, barium-cerium oxides can be used, which is the same as the hydrogen sensor 10 in Embodiment 1.

In the hydrogen sensor 60 of this embodiment, when a constant voltage is applied between the first electrode 61 as the cathode and the second electrode 62 as the anode, the hydrogen contained in a gas to be measured is dissociated in the second electrode 62, becomes protons, is conducted in the solid electrolyte 11, becomes hydrogen or hydrocarbon in the first electrode 61, and is released. Thus, charges move in the solid electrolyte 11 in the form of protons, so that a current flows. See FIG. 17B.

Hereinafter, the results of measuring hydrogen concentrations of a gas to be measured with the hydrogen sensor 60 of this embodiment will be described. Herein, sintered $BaZr_{0.4}Ce_{0.4}In_{0.2}O_{3-\alpha}$ was used for the solid electrolyte 11. The size of the solid electrolyte 11 was 10 mm square and 0.5 mm in thickness.

As a gas to be measured, a propane gas was used that was flowing at 0.2 liter/min and to which 0 to 5 vol % of hydrogen was added at 1 liter/min.

Figure 18:
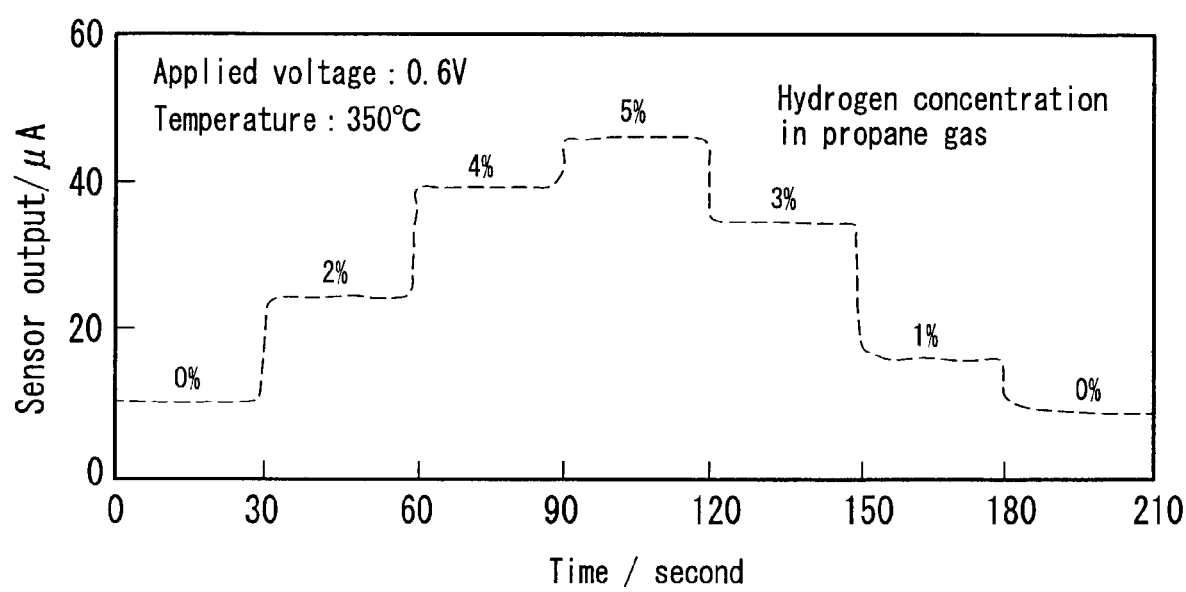
FIG. 18 is a graph showing the relationship between the sensor output and the leak current in the hydrogen sensor of Embodiment 10.

FIG. 18 shows a graph of temporal changes of the sensor outputs when the voltage applied between the first electrode 61 and the second electrode 62 is 0.6V. In the graph of FIG. 18, the % representation along the broken line is the amount of added hydrogen (vol %) at the time when each sensor output (μA) was obtained. In this embodiment, the solid electrolyte 11 was heated by the heater 14, and the temperature of the hydrogen sensor 60 was kept at 350° C.

As seen from FIG. 18, hydrogen concentrations in a high concentration region of 0 to 5 vol % were detected stably in a reducing atmospheric of propane gas when the sensor temperature was 350° C. In addition, when butane gas was used instead of the propane gas, the hydrogen concentration was detected with a high sensitivity, which is the same result as in the case of the propane gas.

Embodiment 11

Figure 19A:
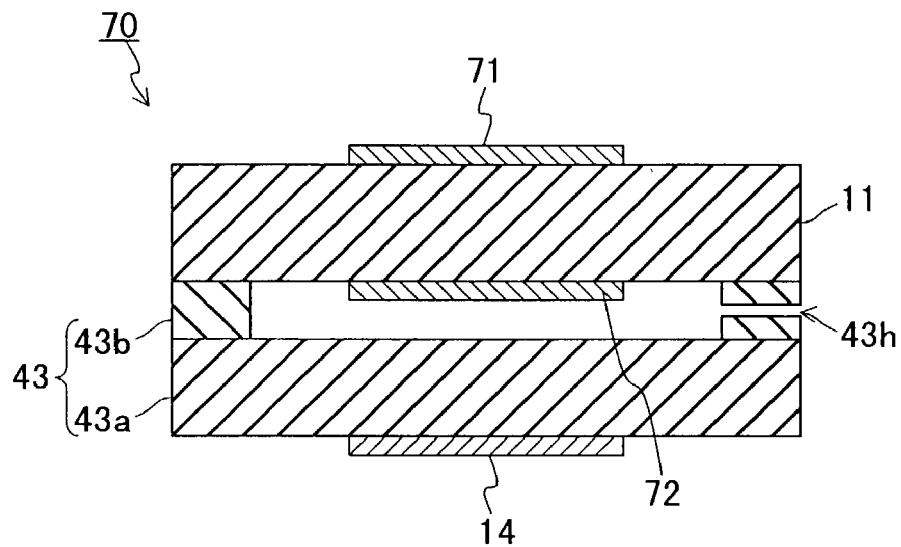
FIG. 19A is a cross-sectional view showing the structure of a hydrogen sensor of Embodiment 11.
Figure 19B:
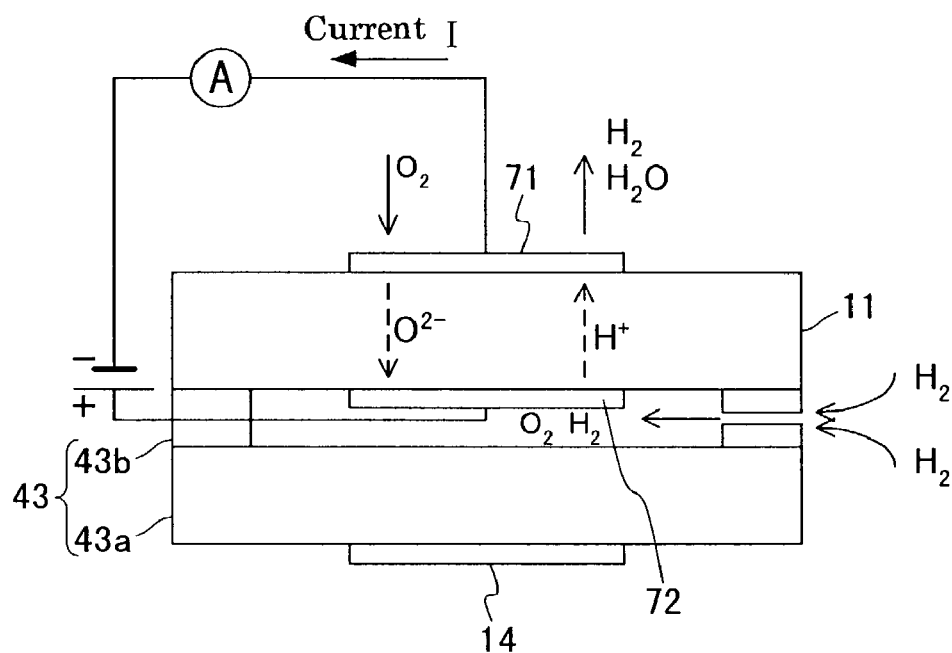
FIG. 19B is a schematic view showing the operation of the hydrogen sensor of Embodiment 11.

FIG. 19A shows a cross-sectional view of the structure of a hydrogen sensor 70 of this embodiment, and FIG. 19B is a schematic view showing the operation thereof. A solid electrolyte 11 is made of an ion conductor that conducts protons (H$^+$) and oxide ions (O$^{2-}$). A first electrode 71 and a second electrode 72 are opposed to each other on the upper and lower surfaces of the solid electrolyte 11 to conduct ions in the solid electrolyte 11. Controlling means 43 for restricting the amount of the hydrogen that reaches the second electrode 72 includes a forsterite substrate 43a and a glass 43b, which are formed so as to cover the second electrode 72. A through-hole 43h is formed in the glass 43b, and a gas to be measured containing hydrogen is introduced from this hole to the second electrode 72. The configuration of the controlling means 43 is not limited thereto, and any other configurations can be used, as long as they can restrict the amount of the hydrogen that reaches the second electrode 72. A heater 14 for heating the solid electrolyte 11 is provided on the lower surface of the glass 43b. The heater 14 can be made of sintered platinum that has been patterned, for example.

The hydrogen sensor 70 is a so-called limiting current type sensor. In this sensor, a constant voltage is applied between the first electrode 71 and the second electrode 72 so that a current generated by the conduction of oxide ions flows steadily between the first electrode 71 and the second electrode 72. In this case, the controlling means 43 restricts hydrogen from passing through the through-hole 43h, and the amount of that hydrogen and the amount of the hydrogen that passes through the solid electrolyte 11 and is released from the second electrode 72 reaches an equilibrium. The amount of the hydrogen at this equilibrium is substantially proportional to the hydrogen concentration of the gas to be measured. The limiting current flowing between the first electrode 71 and the second electrode 72 at the equilibrium is substantially proportional to the amount of the hydrogen at the equilibrium. Therefore, the hydrogen concentration of the gas to be measured can be detected precisely by measuring the limiting current. See FIG. 19B.

For the solid electrolyte 11, ion conductors that conduct protons ($H^+$) and oxide ions ($O^{2-}$) such as $BaCe_{0.8}Gd_{0.2}O_{3-\alpha}$, $BaZr_{0.4}Ce_{0.4}Gd_{0.2}O_{3-\alpha}$, $BaZr_{0.4}Ce_{0.4}Yb_{0.2}O_{3-\alpha}$, and $BaZr_{0.2}Ce_{0.65}Gd_{0.15}O_{3-\alpha}$ can be used. The first electrodes 71 and the second electrode 72 are made of platinum.

Hereinafter, the results of measuring hydrogen concentrations of a gas to be measured with the hydrogen sensor 70 of this embodiment will be described. Herein, sintered $BaZr_{0.4}Ce_{0.4}In_{0.2}O_{3-\alpha}$ was used for the solid electrolyte 11. The size of the solid electrolyte 11 was 10 mm square and 0.5 mm in thickness. The first electrode 71 and the second electrode 72 were formed by firing a platinum paste.

Figure 20:
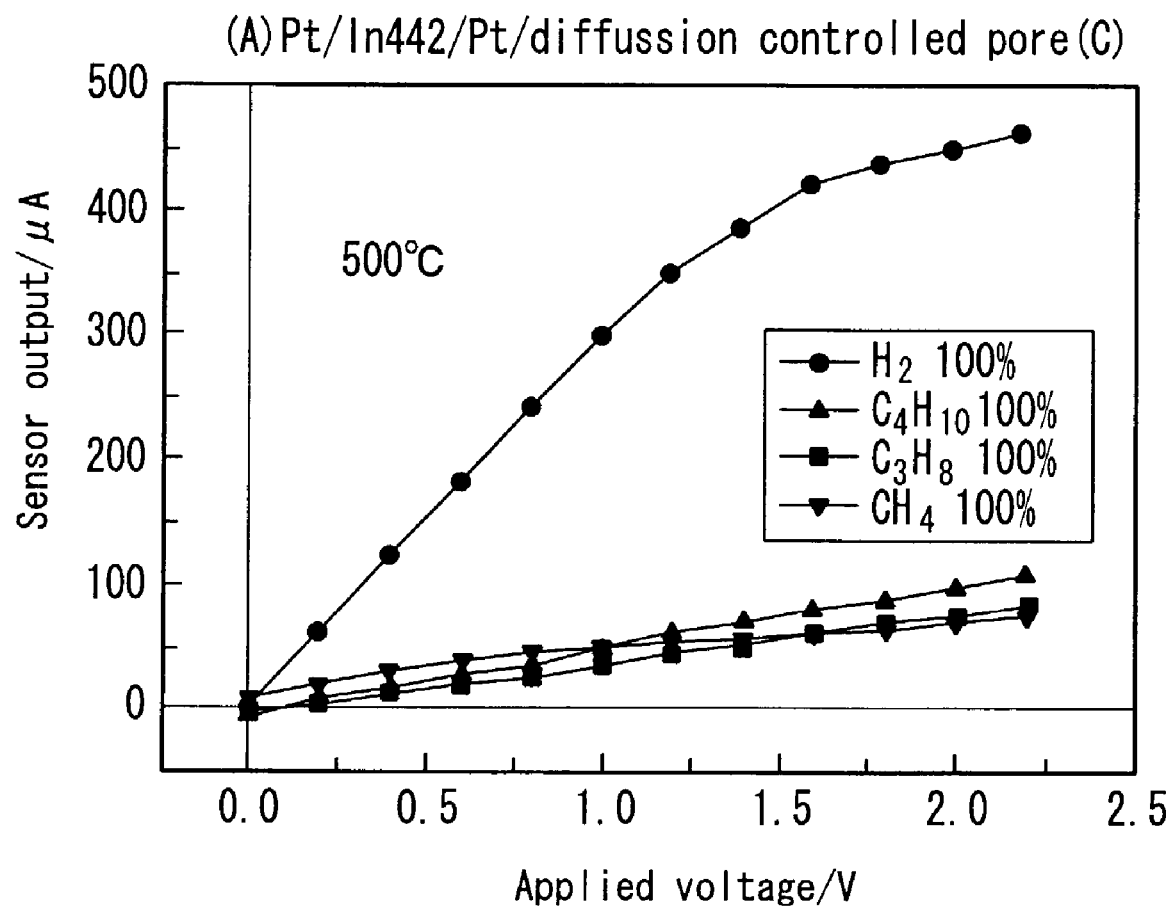
FIG. 20 is a graph showing the relationship between the sensor output and the voltage applied to the electrodes in the hydrogen sensor of Embodiment 11.

As a gas to be measured, hydrogen, butane gas, propane gas, and methane gas were used that were flowing at 1 liter/min and to which 0 to 10 vol % of hydrogen was added at 1 liter/min. FIG. 20 shows the relationship between the value of the current flowing between the first electrode 71 and the second electrode 72 of the hydrogen sensor 70 (sensor output) and the voltage applied between the first electrode 71 and the second electrode 72. In this embodiment, the solid electrolyte 11 was heated by the heater 14 such that the temperature of the sensor was 500° C. for measurement (the temperature shown in the graph of FIG. 20 is the temperature of the sensor at the time of detection of the hydrogen concentrations).

As seen from FIG. 20, hydrogen concentrations in a high concentration region of 0 to 5 vol % were detected in a reducing atmosphere of hydrogen, butane gas, propane gas, and methane gas when the temperature of the sensor was 500° C. Since the limiting current was detected, the gradient of the current with respect to the hydrogen concentration was increased, and the detection precision of the hydrogen concentration was improved. As for the responsiveness, the time until the current value reached 90% of the final current value was about 10 seconds, which is a good responsiveness.

Furthermore, in this embodiment, in order to investigate the influence of the mixture of other types of gases, 2 vol % each of carbon monoxide, nitrogen monoxide, carbon dioxide, and water vapor saturated at room temperature were added to the gas to be measured, and an increase or a decrease of the current value was observed. Then, there was substantially no variation in the current value, and the current values measured were very stable.

In this embodiment, the first electrode 71 and the second electrode 72 are made of platinum, but may be made of other material, as long as the first electrode 71 and the second electrode 72 are made of a material having a catalytic effect with respect to an oxidation reaction of hydrogen and the same material. More specifically, a metal containing at least one selected from the group consisting of platinum, gold, silver, palladium, and ruthenium can be used, and for example, a pure metal of gold, silver, palladium or ruthenium can be used. The first electrode 71 and the second electrode 72 can be made of a material being capable of preventing oxygen from being ionized, such as aluminum, copper and nickel. Furthermore, the first electrode 71 and the second electrode 72 can be formed by firing a metal paste, physical methods such as sputtering, or CVD (chemical vapor deposition method).

The hydrogen sensor 70 of this embodiment can detect stably and easily hydrogen concentrations in a high concentration region of 0 to 5 vol % in the reducing atmosphere with excellent responsiveness and hydrogen selectivity. Furthermore, the hydrogen sensor 70 is inexpensive because of its simple structure, and has high reliability.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A method of detecting a hydrogen concentration comprising:
    placing a hydrogen sensor in an atmosphere for detecting the hydrogen concentration, the hydrogen sensor having a solid electrolyte and a first and a second electrode provided on a surface of the solid electrolyte;
    controlling a temperature of the hydrogen sensor;
    applying a voltage between the first and the second electrodes; and
    measuring a current flowing between the first electrode and the second electrode to detect a hydrogen concentration,
    wherein the solid electrolyte includes an ion conductor that conducts protons and oxide ions,
    the ion conductor is made of a barium-cerium oxide expressed by a general formula $BaCe_{1-x-y}L_xM_yO_{3-\alpha}$, where L is a tetravalent element, M is a trivalent element.
    $0<x<1, 0<Y<1$, and $\alpha$ represents a deficiency of oxygen,
    $T \cdot C_O/(C_O+C_H) \leq 2.7 \times 10^{-3}$ (S/cm) is satisfied at a temperature in the range from 200 to 450° C., where $C_O$ is a conductance of the oxide ions and $C_H$ is a conductance of the protons, and T (S/cm) is a conductivity of the ion conductor,
    a temperature of the sensor is controlled to be in the range from 200 to 450° C., and
    the voltage applied between the first and the second electrodes is controlled so that an electrolytic field intensity formed in the solid electrolyte is controlled to be 1.11 V/mm or less.

2. The method of detecting a hydrogen concentration according to claim 1, wherein
    the electrolytic field intensity is controlled to be 0.044 to 1.11 V/mm.

3. The method of detecting a hydrogen concentration according to claim 1, wherein the first electrode is capable of preventing oxygen from being ionized.

4. The method of detecting a hydrogen concentration according to claim 3, wherein
    the first electrode contains at least one element selected from the group consisting of aluminum, copper and nickel.

5. The method of detecting a hydrogen concentration according to claim 3, wherein
    the first electrode is used as a cathode.

6. The method of detecting a hydrogen concentration according to claim 3, further comprising:
    a controlling member for restricting an amount of hydrogen that reaches the second electrode,
    wherein at least one of the first and the second electrodes is capable of preventing oxygen from being ionized.

7. The method of detecting a hydrogen concentration according to claim 1, wherein L is Zr, and M is In, Gd, or Yb.

* * * * *

UNITED STATES PATENT AND TRADEMARK OFFICE
CERTIFICATE OF CORRECTION

PATENT NO. : 7,235,171 B2 Page 1 of 1
APPLICATION NO. : 10/202265
DATED : June 26, 2007
INVENTOR(S) : Taniguchi It is certified that error appears in the above-identified patent and that said Letters Patent is hereby corrected as shown below:

Column 20, line 28(claim 1): "element. " should read --element, --.

Signed and Sealed this

Sixth Day of November, 2007

JON W. DUDAS
*Director of the United States Patent and Trademark Office*